United States Patent
Ashford, II et al.

(10) Patent No.: US 11,881,549 B2
(45) Date of Patent: Jan. 23, 2024

(54) PHYSICAL VAPOR DEPOSITED ELECTRODE FOR ELECTROCHEMICAL SENSORS

(71) Applicant: EASTMAN CHEMICAL COMPANY, Kingsport, TN (US)

(72) Inventors: Dennis Lee Ashford, II, Johnson City, TN (US); Daniel Patrick Puzzo, Johnson City, TN (US); Spencer Erich Hochstetler, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 474 days.

(21) Appl. No.: 16/625,000

(22) PCT Filed: Jun. 5, 2018

(86) PCT No.: PCT/US2018/035955
§ 371 (c)(1),
(2) Date: Dec. 20, 2019

(87) PCT Pub. No.: WO2018/236572
PCT Pub. Date: Dec. 27, 2018

(65) Prior Publication Data
US 2020/0220168 A1 Jul. 9, 2020

Related U.S. Application Data

(60) Provisional application No. 62/643,305, filed on Mar. 15, 2018, provisional application No. 62/523,387, filed on Jun. 22, 2017.

(51) Int. Cl.
*H01M 4/38* (2006.01)
*G01N 27/327* (2006.01)
(Continued)

(52) U.S. Cl.
CPC .......... *H01M 4/38* (2013.01); *G01N 27/3277* (2013.01); *G01N 33/48707* (2013.01); *H01M 4/0426* (2013.01); *H01M 4/366* (2013.01)

(58) Field of Classification Search
CPC ...... H01M 4/38; H01M 4/0426; H01M 4/366; G01N 27/3277; G01N 33/48707
See application file for complete search history.

(56) References Cited

U.S. PATENT DOCUMENTS

| 3,264,074 A | * | 8/1966 | Jones | H01J 17/492 |
| | | | | 428/653 |
| 4,752,360 A | | 6/1988 | Jasinski | |

(Continued)

FOREIGN PATENT DOCUMENTS

| CN | 1779455 A | 5/2006 |
| CN | 101393160 A | 3/2009 |

(Continued)

OTHER PUBLICATIONS

Notification of Transmittal of the International Search Report and the Written Opinion of the International Searching Authority, or the Declaration dated Aug. 29, 2018 received in International Application No. PCT/US2018/035955.

(Continued)

*Primary Examiner* — Alexander Satanovsky
*Assistant Examiner* — Sharah Zaab
(74) *Attorney, Agent, or Firm* — Michael K. Carrier

(57) ABSTRACT

An electrochemical electrode and method for making same that provides enhanced characteristics for use in biosensors, such as blood glucose sensors. The electrode comprises a substrate, a conductive layer deposited on the substrate, and a resistive material layer deposited on the conductive layer.

(Continued)

The conductive layer comprises nickel and chromium, and the resistive material layer comprises carbon and a carbon-nitrogen species.

20 Claims, 9 Drawing Sheets

(51) Int. Cl.
 *G01N 33/487* (2006.01)
 *H01M 4/04* (2006.01)
 *H01M 4/36* (2006.01)

(56) References Cited

U.S. PATENT DOCUMENTS

| | | |
|---|---|---|
| 5,227,211 A * | 7/1993 | Eltoukhy .............. G01N 3/56 |
| | | 428/408 |
| 5,429,895 A | 7/1995 | Lian et al. |
| 5,484,517 A | 1/1996 | Hopson, Jr. |
| 5,837,354 A | 11/1998 | Ogisu et al. |
| 6,013,170 A | 1/2000 | Meade |
| 6,096,426 A | 8/2000 | Moker'I |
| 6,103,033 A | 8/2000 | Say et al. |
| 6,171,714 B1 | 1/2001 | Bergkessel et al. |
| 6,187,479 B1 | 2/2001 | Liu |
| 6,332,900 B1 | 12/2001 | Muffoletto et al. |
| 6,352,781 B1 | 3/2002 | Lohwasser et al. |
| 6,388,366 B1 | 5/2002 | Pryor |
| 6,468,657 B1 | 10/2002 | Hou et al. |
| 6,484,045 B1 | 11/2002 | Holker et al. |
| 6,572,936 B1 | 6/2003 | Domoto et al. |
| 6,758,957 B1 | 7/2004 | Zhou et al. |
| 6,821,624 B2 | 11/2004 | Utsumi et al. |
| 6,824,974 B2 | 11/2004 | Pisharody et al. |
| 6,828,040 B2 | 12/2004 | Cunningham et al. |
| 6,855,243 B2 | 2/2005 | Khan |
| 6,859,310 B2 | 2/2005 | Simpson et al. |
| 6,869,676 B2 | 3/2005 | Burger et al. |
| 6,921,469 B2 | 7/2005 | Larsen |
| 7,018,523 B2 | 3/2006 | Meade |
| 7,057,805 B2 | 6/2006 | Phillips et al. |
| 7,063,776 B2 | 6/2006 | Huang |
| 7,139,162 B2 | 11/2006 | Michel et al. |
| 7,216,661 B2 | 5/2007 | Welty et al. |
| 7,416,786 B2 | 8/2008 | Oda et al. |
| 7,465,597 B2 | 12/2008 | Wegner et al. |
| 7,510,786 B2 | 3/2009 | Veerasamy et al. |
| 7,556,724 B2 | 7/2009 | Huang |
| 7,563,346 B2 | 7/2009 | Chen |
| 7,563,509 B2 | 7/2009 | Chen |
| 7,611,751 B2 | 11/2009 | Elers |
| 7,662,880 B2 | 2/2010 | Xia et al. |
| 7,688,167 B2 | 3/2010 | Paranjpye et al. |
| 7,781,322 B2 | 8/2010 | Ku et al. |
| 7,824,620 B2 | 11/2010 | Bau et al. |
| 7,858,147 B2 | 12/2010 | Wu et al. |
| 7,919,151 B2 | 4/2011 | Deng et al. |
| 7,939,172 B2 | 5/2011 | Gorokhovsky et al. |
| 8,192,820 B2 | 6/2012 | Asplund et al. |
| 8,287,719 B2 | 10/2012 | Bhattacharya |
| 8,309,362 B2 | 11/2012 | Palleschi et al. |
| 8,372,524 B2 | 2/2013 | Chang et al. |
| 8,378,335 B2 | 2/2013 | Yamazaki et al. |
| 8,420,363 B2 | 4/2013 | Wang et al. |
| 8,424,763 B2 | 4/2013 | Charlton et al. |
| 8,440,563 B2 | 5/2013 | Matsumoto et al. |
| 8,493,711 B2 | 7/2013 | Seymour |
| 8,503,162 B2 | 8/2013 | Seymour |
| 8,574,679 B2 | 11/2013 | Kawabata |
| 8,603,308 B2 * | 12/2013 | Bhullar .............. G01N 33/5438 |
| | | 204/403.01 |
| 8,603,608 B2 | 12/2013 | Shin et al. |
| 8,603,825 B2 | 12/2013 | Chua et al. |
| 8,613,822 B2 | 12/2013 | Van Nutt et al. |
| 8,623,153 B2 | 1/2014 | Pruneri et al. |
| 8,685,802 B2 | 4/2014 | Kelber et al. |
| 8,795,856 B2 | 8/2014 | Kaiju et al. |
| 8,809,843 B2 | 8/2014 | McKone et al. |
| 8,974,983 B2 | 3/2015 | Himeno et al. |
| 8,980,073 B2 | 3/2015 | Pourmand et al. |
| 9,105,378 B2 | 8/2015 | Kim et al. |
| 9,122,336 B1 | 9/2015 | Lai |
| 9,159,924 B2 | 10/2015 | Lee et al. |
| 9,222,909 B2 | 12/2015 | Watanabe et al. |
| 9,343,533 B2 | 5/2016 | Seacrist et al. |
| 9,418,796 B2 | 8/2016 | Yoshimura et al. |
| 9,506,890 B2 | 11/2016 | Hochstetler et al. |
| 9,567,680 B2 | 2/2017 | Kim et al. |
| 9,643,842 B2 | 5/2017 | Tan et al. |
| 10,569,330 B2 | 2/2020 | King et al. |
| 10,808,273 B2 | 10/2020 | Goodwin et al. |
| 11,624,723 B2 | 4/2023 | Hochstetler et al. |
| 11,630,075 B2 | 4/2023 | Hochstetler et al. |
| 2002/0044405 A1 * | 4/2002 | Muffoletto .......... H01M 4/0428 |
| | | 361/502 |
| 2004/0039928 A1 | 2/2004 | Elbe et al. |
| 2004/0086717 A1 | 5/2004 | Sasaki et al. |
| 2004/0118705 A1 | 6/2004 | Khan |
| 2005/0012115 A1 * | 1/2005 | Grueger .............. G01N 27/414 |
| | | 257/192 |
| 2005/0199585 A1 | 9/2005 | Wang et al. |
| 2005/0284758 A1 | 12/2005 | Funke et al. |
| 2006/0068392 A1 | 3/2006 | Kimura et al. |
| 2006/0175199 A1 | 8/2006 | Huang |
| 2006/0269826 A1 | 11/2006 | Katz et al. |
| 2007/0193882 A1 | 8/2007 | Dai et al. |
| 2007/0290591 A1 | 12/2007 | Lykowski et al. |
| 2008/0083618 A1 | 4/2008 | Neel et al. |
| 2009/0071837 A1 | 3/2009 | Fredenberg et al. |
| 2010/0129615 A1 | 5/2010 | Chizik et al. |
| 2010/0181869 A1 | 7/2010 | Pereira da Cunha et al. |
| 2010/0213079 A1 | 8/2010 | Willis |
| 2010/0291464 A1 | 11/2010 | Elhamid et al. |
| 2011/0272295 A1 | 11/2011 | Lee et al. |
| 2012/0118735 A1 * | 5/2012 | Kim .................. G01N 27/3272 |
| | | 204/403.02 |
| 2012/0164434 A1 | 6/2012 | Ramadas et al. |
| 2012/2222958 | 9/2012 | Pourmand et al. |
| 2012/0299175 A1 * | 11/2012 | Tran .................. G11C 13/0019 |
| | | 257/E23.09 |
| 2012/0301816 A1 | 11/2012 | Lee |
| 2012/0328906 A1 | 12/2012 | Kwon et al. |
| 2013/0052475 A1 | 2/2013 | Kim et al. |
| 2013/0090652 A1 | 4/2013 | Jenson |
| 2015/0144507 A1 | 5/2015 | Bain |
| 2015/0168336 A1 | 6/2015 | Diguet et al. |
| 2015/0311071 A1 * | 10/2015 | Ebata ................ H01L 29/66969 |
| | | 257/43 |
| 2016/0103123 A1 | 4/2016 | Holmes et al. |
| 2016/0164010 A1 | 6/2016 | Berger et al. |
| 2016/0169827 A1 * | 6/2016 | Hochstetler .......... G01N 33/553 |
| | | 204/403.14 |
| 2016/0329209 A1 * | 11/2016 | Zhuang ................ C04B 35/645 |
| 2017/0153200 A1 | 6/2017 | Komoto et al. |
| 2017/0184534 A1 | 6/2017 | Goodwin et al. |
| 2020/0220168 A1 | 7/2020 | Ashford, II et al. |
| 2020/0271612 A1 | 8/2020 | Hochstetler et al. |
| 2020/0271613 A1 | 8/2020 | Hochstetler et al. |

FOREIGN PATENT DOCUMENTS

| | | |
|---|---|---|
| CN | 101530327 A | 9/2009 |
| CN | 101839884 A | 9/2010 |
| CN | 2016-97658 U | 1/2011 |
| CN | 102021365 A | 4/2011 |
| CN | 103743805 A | 4/2014 |
| EP | 0176313 A2 | 4/1986 |
| EP | 1347302 A2 | 9/2003 |
| ES | 2186494 A1 | 5/2003 |
| JP | 2001-341227 A | 12/2001 |
| JP | 2003-096577 A | 4/2003 |
| JP | 2003-315302 A | 11/2003 |

(56) References Cited

FOREIGN PATENT DOCUMENTS

| | | | |
|---|---|---|---|
| JP | 2004-504604 A | 2/2004 | |
| JP | 2004-217977 A | 8/2004 | |
| JP | 2014-153280 A | 8/2014 | |
| KR | 101303590 B1 | 9/2013 | |
| KR | 1397444 B1 | 5/2014 | |
| KR | 101619109 A | 5/2016 | |
| KR | 102013836 | 8/2019 | |
| TW | I244550 B | 12/2005 | |
| TW | M286367 | 1/2006 | |
| TW | 201504035 A | 2/2017 | |
| WO | WO 1996-012315 A | 4/1996 | |
| WO | WO 1999-30152 A1 | 6/1999 | |
| WO | WO 01-58348 A2 | 8/2001 | |
| WO | WO 2010-010211 A3 | 1/2010 | |
| WO | WO 2010-122270 A1 | 10/2010 | |
| WO | WO 2010-123802 A2 | 10/2010 | |
| WO | WO 2016-100266 A1 | 6/2016 | |
| WO | WO 2017-112688 A1 | 6/2017 | |

OTHER PUBLICATIONS

Stanishevsky, Andrei et al., "Quaziamorphous Carbon and Carbon Nitride Films Deposited from the Plasma of Pulsed Cathodic Arc Discharge", Chaos, Solutions and Fractals, vol. 10, No. 12, Jan. 1, 1999, pp. 2045-2066.
Lee, Sung Pil, "Synthesis and Characterization of Carbon Nitride Films for Micro Humidity Sensors", Sensors, vol. 8, No. 3, Mar. 3, 2008, pp. 1508-1518.
Onoprienko, A., et al. "Role of microstructure in forming thin carbon film properties", Diamond Related Materials. 1994, vol. 3, 1132-1136.
Cho, N. H., et al. "Chemical structure and physical properties of diamond-like amorphous carbon films prepared by magnetron sputtering", Journal of Materials Research, 1990, vol. 5, Issue 11, pp. 2543-2554.
USPTO Office Action dated Feb. 14, 2023 in co-pending U.S. Appl. No. 16/305,594.
Ghamousse, et al. Screen-printed carbon electrode modified on its surface with amorphouse carbon nitride thin film: Electrochemical and morphological study, Electrochimica Acta 52, 2007, 5053-5061.
Co-pending U.S. Appl. No. 14/572,290, filed Dec. 16, 2014, Hochstetler et al.
USPTO Office Action dated Apr. 17, 2015 in co-pending U.S. Appl. No. 14/572,290.
Co-pending U.S. Appl. No. 14/724,563, filed May 28, 2015, Hochstetler et al. Publication No. 2016-0169827. Now U.S. Pat. No. 9,506,890.
USPTO Office Action dated Aug. 17, 2015 in co-pending U.S. Appl. No. 14/724,563.
USPTO Office Action dated Mar. 1, 2016 in co-pending U.S. Appl. No. 14/724,563.
Notification of Transmittal of the International Search Report and the Written Opinion of the International Searching Authority, or the Declaration dated Mar. 14, 2016 for International Application No. PCT/US2015/065685.
Notice of Allowance and Fee(s) due dated Jul. 25, 2016 received in co-pending U.S. Appl. No. 14/724,563.
Co-pending U.S. Appl. No. 16/305,594, filed Jun. 1, 2017, Hochstetler et al.
Notification of Transmittal of the International Search Report and the Written Opinion of the International Searching Authority, or the Declaration dated Aug. 14, 2017 for International Application No. PCT/US2017/035353.
Written Opinion of the International Preliminary Examining Authority, dated Aug. 27, 2018 received in International Application No. PCT/US2017/049312.
USPTO Office Action dated Jun. 17, 2021 in co-pending U.S. Appl. No. 16/305,594.
USPTO Office Action dated Jan. 10, 2022 in co-pending U.S. Appl. No. 16/305,594.
USPTO Office Action dated Apr. 25, 2022 in co-pending U.S. Appl. No. 16/305,594.
USPTO Office Action dated Aug. 4, 2022 received in co-pending U.S. Appl. No. 16/332,400.
Inconell Alloy 600 data sheet, Sep. 2008.
Inconell Alloy 617 data sheet, Mar. 2005.
Nickel & High Temperature Alloys Chart (Year: 2016).
Taiwan Office Action and Search Report, ROC (Taiwan) Patent Application No. 104142335; Date of Completion of Search Aug. 24, 2019.
Taiwan Office Action and Search Report, ROC (Taiwan) Patent Application No. 106130541; Date of Completion of Search Dec. 22, 2020.
Taiwan Office Action and Search Report, ROC (Taiwan) Patent Application No. 107120347; Date of Completion of Search Aug. 13, 2021.
USPTO Notice of Allowance dated Oct. 19, 2022 in co-pending U.S. Appl. No. 16/332,400.
USPTO Office Action dated Oct. 27, 2022 in co-pending U.S. Appl. No. 16/305,594.
Notice of Allowance and Fee(s) due dated Nov. 9, 2022 received in co-pending U.S. Appl. No. 16/332,394.
Notice of Allowance and Fee(s) due dated Mar. 7, 2023 received in co-pending U.S. Appl. No. 16/332,394.
Notification of Transmittal of the International Search Report and the Written Opinion of the International Searching Authority, or the Declaration dated Nov. 8, 2017 received in International Application No. PCT/US2017/049312.
Notification of Transmittal of the International Search Report and the Written Opinion of the International Searching Authority, or the Declaration dated Nov. 8, 2017 received in International Application No. PCT/US2017/049281.
Co-pending U.S. Appl. No. 16/332,394, filed Mar. 12, 2019; Hochstetler et al., now US Patent Publication No. 2020-0271612.
Co-pending U.S. Appl. No. 16/332,400, filed Mar. 12, 2019; Hochstetler et al., now US Patent Publication No. 2020-0271613.
USPTO Office Action dated Jun. 9, 2021 received in co-pending U.S. Appl. No. 16/332,400.
USPTO Office Action dated Sep. 20, 2021 received in co-pending U.S. Appl. No. 16/332,400.
USPTO Office Action dated Jan. 28, 2022 received in co-pending U.S. Appl. No. 16/332,400.
USPTO Office Action dated May 17, 2022 received in co-pending U.S. Appl. No. 16/332,400.
USPTO Office Action dated Jun. 3, 2022 received in co-pending U.S. Appl. No. 16/625,000.
USPTO Office Action dated Jul. 21, 2022 received in co-pending U.S. Appl. No. 16/332,394.
ASTM D 1003-00; Standard Test Methods for Haze and Luminous Transmittance of Transparent Plastics[1].
ASTM F 1711-96 Standard Practice for Measuring Sheet Resistance of Thin Film Conductors for Flat Panel Display Manufacturing Using a Four-Point Probe Method.
Marioli, Juan M et al., "Electrochemical detection of carbohydrates at nickel-copper and nickel-chromium-iron alloy electrodes", Electroanalysis, vol. 5, No. 1, Jan. 1, 1993, pp. 11-15.
Narayan, Roger, "Nanostructured diamondlike carbon thin films for medical applications", Materials Science and Engineering, C, vol. 25, p. 405-416.
Onoprienko, A., "Electrical Resistivity and Real Structure of Magnetron-Sputtered Carbon Films", The Future Material for Advanced Technology Applications, Topics Appl. Phys. 100, 2007, pp. 175-186.
Response to the Communication Pursuant to Rules 161(1) and 162 EPC (dated Apr. 25, 2019) filed in the European Patent Office on Aug. 6, 2019 in Regional Phase EP 17780240.2 based on PCT/US2017/049312.
Response to the Communication Pursuant to Art. 94(3) EPC (dated Mar. 28, 2020) filed in the European Patent Office on Jul. 2, 2020 in Regional Phase EP 17780240.2 based on PCT/US2017/049312.
Response to the Communication Pursuant to Art. 94(3) EPC (dated Oct. 15, 2020) filed in the European Patent Office on Apr. 23, 2021 in Regional Phase EP 17780240.2 based on PCT/US2017/049312.

(56) References Cited

OTHER PUBLICATIONS

Request for International Preliminary Examination and Response to Written Opinion filed in the European Patent Office on Mar. 6, 2018 in PCT International Application No. PCT/US2017/049312.

Xu et al., "Making co-condensed amorphous carbon/g-C3N4 composites with improved visible-light photocatalytic H2-production performance using Pt as cocatalyst", El Sevier, 2017, Carbon, vol. 118, pp. 241-249.

Notice of Allowance and Fee(s) due dated Sep. 11, 2023 received in co-pending U.S. Appl. No. 16/305,594.

USPTO Notice of Allowance dated Feb. 15, 2023 in co-pending U.S. Appl. No. 16/332,400.

\* cited by examiner

PHYSICAL VAPOR DEPOSITED ELECTRODE FOR ELECTROCHEMICAL SENSORS

CROSS-REFERENCE TO RELATED APPLICATION(S)

This application is a national stage filing under 35 USC § 371 of International Application Number PCT/US2018/035955, filed on Jun. 5, 2018, which claims the benefit of U.S. Provisional Application No. 62/523,387, filed on Jun. 22, 2017 and U.S. Provisional Application No. 62/643,305, filed on Mar. 15, 2018, the entire disclosures of which are incorporated by reference herein.

BACKGROUND

Field of the Invention

The present invention is generally related to electrodes, for example, physical vapor deposited thin film electrodes such as those found in biosensors. More particularly, the present invention is related to electrodes formed with non-noble metal alloys, for example, those found in biosensor components.

Description of the Related Art

Biosensors for use in analyzing biological samples are becoming increasingly prevalent. For example, with the rise in cases of diabetes in the world's population, the need for biosensors for measuring blood glucose has risen dramatically. Such biosensors are generally known as glucometers and operate by having a user place a drop of blood on a test-strip associated with the glucometer. The test-strip is configured to be reactive to the amount of glucose in the drop of blood, such that the glucometer can detect and display a glucose level of the user's blood.

The test-strips for glucometer-type biosensors are generally formed with two or more electrodes (e.g., a working electrode and a counter electrode) formed on a substrate. In addition, a bio-reactant that reacts with a biological sample, e.g., an enzyme (e.g., glucose oxidase, glucose dehydrogenase, or the like), and a mediator (e.g., ferricyanide, ruthenium complexes, osmium complexes, quinones, phenothiazines, phenoxazines, or the like) will be formed on one or both electrodes, e.g., the working electrode. In operation of a glucometer-type biosensor, a drop of blood will be applied to a test-strip. Thereafter, an electrochemical reaction proportional to the amount of glucose in the blood will take place on the working electrode. In more detail, glucose first reacts with the bio-reactant, e.g., enzyme (glucose oxidase, glucose dehydrogenase, or the like) and sometimes an enzyme cofactor (PQQ, FAD, or the like) and is oxidized to gluconic acid. The bio-reactant, e.g., enzyme, cofactor, or enzyme-cofactor complex, is temporarily reduced by two electrons transferred from glucose to the enzyme, cofactor, or enzyme-cofactor complex. Next, the reduced bio-reactant, e.g., enzyme, cofactor, or enzyme-cofactor complex, reacts with the mediator, transferring a single electron to each of two mediator species (molecules or complexes), in the case of a mediator that is reduced in a one-electron process. When the mediator species are reduced, the enzyme, cofactor, or enzyme-cofactor complex is thus returned to its original oxidation state. Then, the reduced mediators diffuse to the electrode surface where a predetermined and sufficiently oxidizing potential is applied to the biosensor so that the reduced mediators are oxidized back to their original oxidation state. The current that is generated by the oxidation of the mediator species by the biosensor is measured and related proportionally to the amount of glucose in the blood.

The quality of the working electrode plays an important role in an accurate measurement of the glucose level of the blood. Specifically, the reproducibility of the electroactive surface area of the electrode, the lot-to-lot repeatability of the electron transfer kinetics of the electrode in a particular glucose measurement arrangement, and long-term stability of the electrode material while in storage so that the electrochemical signal that arises from the electrode when the assay is in operation are all factors that lead to improved accuracy of blood glucose test strips. Particularly, it is important that the electrical signals resulting from the electro-activity of the electrode is minimized to prevent bias or noise in the measurement and analysis of biological samples. Typically, this is accomplished by using electrode materials that are intrinsically thermodynamically noble, such as gold, palladium, platinum, iridium, and the like. As such, most current glucometers use electrodes formed from substrates coated with palladium, gold, or other noble metals, generally in the purest form commercially feasible, to function as the working electrode, and for ease of manufacturing, often for the counter electrode or a combined counter and reference electrode. Such noble metals are minimally reactive with interfering substances, and as a result, offer enhanced chemical resistance for consistent and accurate measurements. However, the cost of using such noble metals in electrodes can be prohibitive.

There have been some attempts to use electrodes formed with non-noble metals, so as to reduce manufacturing costs of biosensors. However, such non-noble metal electrodes will generally have an electrochemical response (e.g., dose-responses) that deviates significantly from the electrochemical response of electrodes formed with noble metals. Non-precious materials typically are not anodically stable enough to be used for electrochemical test strips because of high background currents generated when operating at typical voltages of biosensors. In addition, non-precious materials typically do not have facile heterogeneous electron transfer with the desired analyte. As such, electrodes formed with non-noble metals are generally inadequate for use as direct replacements for noble metals in test-strips for many types of biosensors. In addition to having a low electrical response, it is also desirable for a biosensor electrode to have sufficient electron transfer kinetics with the mediator. While some suggested non-noble metals have a relatively low electrochemical response (or reasonable anodic stability), they do not also have acceptable electron transfer kinetics with a mediator.

Accordingly, there is a need for an electrode which can provide consistent and accurate measurements, while providing a cost-effective alternative to the use of noble metals, for example, in biosensors. In particular, there is a need for an electrode formed from a non-noble metal alloy that can be used in a biosensor component to consistently and accurately measure biological samples.

SUMMARY

It has been found that non-precious metals can undergo aging phenomenon when exposed to atmospheric conditions resulting in variations in their performance for biosensor applications. It has also been found that electrodes formed by depositing non-precious metals on a substrate film require a sufficient degree of mechanical robustness (e.g., scratch resistance and sufficiently low coefficient of friction) to provide sufficient latitude for manufacturing operations and to achieve adequate performance for biosensor applications. Thus, there is a need for an electrode formed from a non-noble metal alloy that can be used in a biosensor component to consistently and accurately measure biological samples, and which has good mechanical robustness to allow processing and achieve or maintain electrical performance.

One or more embodiments of the present disclosure can relate to an electrode which can comprise a substrate, at least one non-precious metal alloy conductive layer deposited on the substrate, and at least one resistive material layer deposited on the non-precious metal layer. In certain embodiments, the conductive layer can comprise nickel and chromium wherein the combined weight percent of the nickel and chromium in the conductive layer can be at least 24, or at least 25, or at least 50, or at least 60, or at least 70, or at least 80, or at least 90, or at least 95 weight percent, based on the total weight of the conductive layer. In certain embodiments, the conductive layer can comprise nickel in an amount less than 80 weight percent and chromium in an amount of greater than 20 weight percent, based on the total weight of the conductive layer. In certain embodiments, the conductive layer can comprise nickel and chromium wherein the nickel is present in an amount of at least 4, or 5, or 6, or 8 weight percent and the chromium is present in an amount of at least 10 weight percent, based on the weight of the conductive layer. In one embodiment, the thickness of the resistive material layer is less than 20 nm. In certain embodiments, the resistive material layer allows fluid communication between an outside liquid, e.g., saline solution or bio-reactant containing liquid coating, and the conductive layer.

In one embodiment, the conductive layer can comprise nickel and chromium wherein the combined weight percent of the nickel and chromium in the conductive layer can be in the range of 24 or 25 to less than 95 weight percent, at least 10 weight percent chromium, and at least 4, or 5, or 6, or 8 weight percent nickel, based on the total weight of the conductive layer. In addition to nickel and chromium, the conductive layer can also comprise iron wherein the iron is present in an amount greater than 2 weight percent, based on the total weight of the conductive layer equaling 100 weight percent. In embodiments, the conductive layer can comprise 0 to less than 20, or 0 to 17, or 0 to 13, or 0 to 10, or 0 to 9, or 0 to 8, or 0 to 7, or 0 to 6, or 0 to 5, or 0 to 4, or 0 to 3, or 0 to 2, or 0 to 1, or 0 to 0.5, or 0 to 0.1, weight percent molybdenum. In certain embodiments, the conductive layer can comprise 2 to 10, or 2 to 8, or 2 to 7.5, or 2 to 7.0, or 2 to 6.5, or 2.5 to 8, or 2.5 to 7.5, or 2.5 to 7.0, or 2.5 to 6.5, or 3 to 8, or 3 to 7.5, or 3 to 7.0, or 3 to 6.5, or 3.5 to 8, or 3.5 to 7.5, or 3.5 to 7.0, or 3.5 to 6.5, or 4 to 8, or 4 to 7.5, or 4 to 7.0, or 4 to 6.5, or 4.5 to 8, or 4.5 to 7.5, or 4.5 to 7.0, or 4.5 to 6.5, weight percent molybdenum. In certain embodiments, the conductive layer can comprise 2 to 6.5, or 2 to 6.0, or 2 to 5.5, or 2 to 5, or 2 to 4.5, or 2 to 4, or 2.5 to 6.5, or 2.5 to 6.0, or 2.5 to 5.5, or 2.5 to 5, or 2.5 to 4.5, or 2.5 to 4, or 3 to 6.5, or 3 to 6.0, or 3 to 5.5, or 3 to 5, or 3 to 4.5, or 3 to 4, or 3.5 to 6.5, or 3.5 to 6.0, or 3.5 to 5.5, or 3.5 to 5, or 3.5 to 4.5, or 4 to 6.5, or 4 to 6.0, or 4 to 5.5, or 4 to 5, or 4.5 to 6, or 4.5 to 5.5, or 5 to 6, weight percent molybdenum. While most of this disclosure relates to electrodes used as biosensor components, it is contemplated that the electrodes can be used in other end-use applications as well. As a result, any disclosure herein related to electrodes used in biosensors is intended to incorporate herein applicability to all electrodes that this technology could reasonably be applied to by one of ordinary skill in the art.

In a first aspect, the conductive layer can comprise nickel and chromium wherein the combined weight percent of the nickel and chromium in the conductive layer can be at least 50, or at least 60, or at least 70, or at least 80, or at least 90, or at least 95 weight percent, based on the total weight of the conductive layer equaling 100 weight percent, and the thickness of the resistive material layer is less than 20 nm. In one embodiment, the combined weight percent of the nickel and chromium in the conductive layer is in the range of 90 to 100 weight percent, and the thickness of the resistive layer is in the range from 5 to 15 nm.

In embodiments of the first aspect, the weight percent of chromium in the conductive layer is in the range from about 25 to about 95 weight percent, and the balance of the conductive layer is essentially nickel. In embodiments of the first aspect, the resistive material layer comprises amorphous carbon, the weight percent of chromium in the conductive layer is in the range from greater than 50 to about 95 weight percent, and the balance of the conductive layer is essentially nickel.

In a second aspect, the conductive layer can comprise nickel and chromium wherein the combined weight percent of the nickel and chromium in the conductive layer can be at least 25, or at least 50, or at least 60, or at least 70, or at least 80, or at least 90, or at least 95 weight percent, based on the total weight of the conductive layer equaling 100 weight percent, based on the total weight of the conductive layer equaling 100 weight percent. In embodiments of the second aspect, the conductive layer can comprise nickel and chromium wherein the nickel is present in an amount of at least 4, or 5, or 6, or 8 weight percent and the chromium is present in an amount of at least 10 weight percent, based on the weight of the conductive layer. In an embodiment of the second aspect, the conductive layer comprises greater than 20 weight percent chromium. In embodiments of the second aspect, the substrate has a thickness between 25 and 500 µm, the conductive layer has a thickness between 15 and 200 nm, and the resistive material layer has a thickness between 5 and 200 nm, or 5 to 100 nm.

In embodiments of the second aspect, the conductive layer can comprise nickel in the range of less than 80 weight percent, or less than 75 weight percent, and chromium in the range of greater than 20, or greater than 25 weight percent, and wherein the total combined weight percent of the nickel and chromium in the conductive layer is in the range of 90 to 100, or 95 to 100 weight percent, based on the total weight of the conductive layer equaling 100 weight percent.

In embodiments of the second aspect, the weight percent of chromium in the conductive layer is in the range from about 25 to about 95 weight percent, and the balance of the conductive layer is essentially nickel. In other embodiments of the second aspect, the weight percent of chromium in the conductive layer is in the range from about 30 to about 95 weight percent, and the balance of the conductive layer is essentially nickel. In further embodiments of the second aspect, the weight percent of chromium in the conductive layer is in the range from about 40 to about 95 weight percent, and the balance of the conductive layer is essentially nickel. In yet other embodiments of the second aspect, the weight percent of chromium in the conductive layer is in the range from about 50 to about 95 weight percent, and the balance of the conductive layer is essentially nickel. In another embodiment of the second aspect, the weight percent of chromium in the conductive layer is in the range from greater than 50 to about 95 weight percent, and the balance of the conductive layer is essentially nickel.

In embodiments of the second aspect, the resistive layer comprises amorphous carbon. In an embodiment of the second aspect, the resistive layer comprises amorphous carbon, the weight percent of chromium in the conductive layer is in the range from about 25 to about 95 weight percent, and the balance of the conductive layer is essentially nickel. In another embodiment of the second aspect, the resistive layer comprises amorphous carbon, the weight percent of chromium in the conductive layer is in the range from greater than 50 to about 95 weight percent, and the balance of the conductive layer is essentially nickel. In embodiments of the second aspect, the resistive layer comprises amorphous carbon, and the resistive material layer has a thickness between 5 and 30 nm, or between 5 and 20 nm.

In a third aspect, the conductive layer can comprise nickel and chromium wherein the combined weight percent of the nickel and chromium in the conductive layer can be in the range of 24 or 25 to 90 weight percent, or 26 to 89 weight percent, based on the total weight of the conductive layer equaling 100 weight percent. In addition to nickel and chromium, the conductive layer can also comprise iron wherein the weight percent of the iron in the conductive layer can be in the range of greater than 5 weight percent to less than 75 weight percent, or about 6 to about 74 weight percent, based on the total weight of the conductive layer equaling 100 weight percent.

In embodiments of the third aspect, the conductive layer can comprise nickel in the range of greater than 7 weight percent and chromium in the range of greater than 13 to less than 25 or less than 21 weight percent and wherein the total combined weight percent of the nickel and chromium in the conductive layer is in the range of greater than 24 or greater than 25 to less than 90 weight percent, or 26 to 89 weight percent, based on the total weight of the conductive layer equaling 100 weight percent.

In further embodiments of the third aspect, the conductive layer can comprise nickel in the range of 8 to 72 weight percent, chromium in the range of about 14 to about 25 or 14 to about 20 weight percent, and iron in the range of about 6 to about 74 weight percent and wherein the total combined weight percent of the nickel and chromium in the conductive layer is in the range of about 24 or about 25 to about 90 weight percent, or 26 to 89 weight percent, based on the total weight of the conductive layer equaling 100 weight percent.

In certain embodiments of the third aspect, the conductive layer can comprise nickel in the range of 8 to 72 weight percent, chromium in the range of 14 to 25 or 14 to 20 weight percent, and iron in the range of 6 to 74 weight percent, based on the total weight of the conductive layer equaling 100 weight percent.

In certain embodiments of the third aspect, the conductive layer can comprise nickel in the range of 8 to 72 weight percent, chromium in the range of 14 to 25 or 14 to 20 weight percent, iron in the range of 6 to 74 weight percent, and molybdenum in the range of 0 to 10 weight percent, based on the total weight of the conductive layer equaling 100 weight percent, and wherein the conductive layer does not include any other element species that is present in an amount greater than 6 weight percent, or greater than 5 weight percent, or greater than 4 weight percent, or greater than 3 weight percent or greater than 2 weight percent, based on the total weight of the conductive layer equaling 100 weight percent. In one embodiment, the conductive layer further comprises molybdenum in the range of 0.01 to 7.0 weight percent and manganese in the range of 0.01 to 6.0 weight percent, and does not include any other element species that is present in an amount greater than 1.5 weight percent or greater than 1.0 weight percent, based on the total weight of the conductive layer equaling 100 weight percent. In one embodiment, the conductive layer further comprises manganese in the range of 0.01 to 2.0 weight percent, and does not include any other element species that is present in an amount greater than 1.0 weight percent, based on the total weight of the conductive layer equaling 100 weight percent.

In certain embodiments of the third aspect, the conductive layer can comprise nickel in the range of 8 to 72 weight percent, chromium in the range of 14 to 24 or 14 to 20 weight percent, and iron in the range of 6 to 74 weight percent, based on the total weight of the conductive layer equaling 100 weight percent, and wherein the conductive layer further comprises manganese in the range of 0.01 to 2.0 weight percent, silicon in the range of 0.01 to 1.0 weight percent, molybdenum in the range of 0 to 3.0 weight percent, and copper in the range of 0 to 0.5 weight percent, based on the total weight of the conductive layer equaling 100 weight percent. In an embodiment, the conductive layer contains less than 0.2 weight percent of each of the following element species: carbon, sulfur, phosphorous, niobium, cobalt, aluminum, titanium, or boron. In an embodiment, the conductive layer contains none, or is substantially free, of the following element species: niobium, cobalt, aluminum, titanium, or boron. In an embodiment, the conductive layer contains none of the following element species: niobium, cobalt, aluminum, titanium, or boron. In an embodiment, the conductive layer contains less than 0.2 weight percent of each of the following element species: carbon, sulfur, phosphorous, molybdenum, niobium, cobalt, aluminum, titanium, or boron. In an embodiment, the conductive layer contains none, or is substantially free, of the following element species: molybdenum, niobium, cobalt, aluminum, titanium, or boron. In an embodiment, the conductive layer contains none of the following element species: molybdenum, niobium, cobalt, aluminum, titanium, or boron.

In a fourth aspect, the conductive layer can comprise nickel and chromium wherein the combined weight percent of the nickel and chromium in the conductive layer can be in the range of 80 to less than 95 weight percent, or 81 to 94 weight percent, or 82 to 94 weight percent, or 83 to 94 weight percent, or 85 to 94 weight percent, or 86 to 94 weight percent, based on the total weight of the conductive layer equaling 100 weight percent. In addition to nickel and chromium, the conductive layer can also comprise iron wherein the weight percent of the iron in the conductive layer can be in the range of greater than 5 weight percent to less than 12 weight percent, or about 6 to about 11 weight percent, or 6 to 11 weight percent, or 6 to 10 weight percent, or 6 to 9 weight percent, or 7 to 10 weight percent, or 7 to 9 weight percent, or about 8 or about 9 weight percent, based on the total weight of the conductive layer equaling 100 weight percent.

In embodiments of the fourth aspect, the conductive layer can comprise nickel in the range of greater than 70 weight percent and chromium in the range of greater than 13 to less than 20 weight percent and wherein the total combined weight percent of the nickel and chromium in the conductive layer is in the range of greater than 80 to less than 95 weight percent, or 81 to 94 weight percent, or 82 to 94 weight percent, or 83 to 94 weight percent, or 85 to 94 weight percent, or 86 to 94 weight percent, based on the total weight of the conductive layer equaling 100 weight percent.

In further embodiments of the fourth aspect, the conductive layer can comprise nickel in the range of 70 to 81 weight percent, chromium in the range of about 14 to about 19 weight percent, and iron in the range of about 6 to about 11 weight percent and wherein the total combined weight percent of the nickel and chromium in the conductive layer is in the range of about 84 to about 94 weight percent, or 85 to 94 weight percent, or 86 to 94 weight percent, based on the total weight of the conductive layer equaling 100 weight percent.

In certain embodiments of the fourth aspect, the conductive layer can comprise nickel in the range of 70 to 81 weight percent, chromium in the range of 14 to 17 weight percent, and iron in the range of 6 to 11 weight percent, based on the total weight of the conductive layer equaling 100 weight percent.

In certain embodiments of the fourth aspect, the conductive layer can comprise nickel in the range of 72 to 81 weight percent, chromium in the range of 14 to 17 weight percent, and iron in the range of 6 to 11, or 6 to 10, weight percent, based on the total weight of the conductive layer equaling 100 weight percent, and wherein the conductive layer does not include any other element species that is present in an amount greater than 1 weight percent, based on the total weight of the conductive layer equaling 100 weight percent. In one embodiment, the conductive layer further comprises manganese in the range of 0.01 to 1.0 weight percent, and does not include any other element species that is present in an amount greater than 0.5 weight percent, based on the total weight of the conductive layer equaling 100 weight percent.

In certain embodiments of the fourth aspect, the conductive layer can comprise nickel in the range of 72 to 81 weight percent, chromium in the range of 14 to 17 weight percent, and iron in the range of 6 to 11, or 6 to 10, weight percent, based on the total weight of the conductive layer equaling 100 weight percent, and wherein the conductive layer further comprises manganese in the range of 0.01 to 1.0 weight percent, copper in the range of 0.01 to 0.5 weight percent, and silicon in the range of 0.01 to 0.5 weight percent, based on the total weight of the conductive layer equaling 100 weight percent. In an embodiment, the conductive layer contains none or is substantially free of the following element species: molybdenum, niobium, cobalt, aluminum, titanium, phosphorus, or boron, or, if any species is present, such species is in an amount of less than 0.25 weight percent, or less than 0.2 weight percent, or less than 0.1 weight percent, or less than 0.05 weight percent, or trace amounts or less. In an embodiment, the conductive layer contains none, or is substantially free, of the following element species: molybdenum, niobium, cobalt, aluminum, titanium, phosphorus, or boron.

In a fifth aspect, the conductive layer can comprise nickel and chromium wherein the combined weight percent of the nickel and chromium in the conductive layer can be in the range of 24 to 55, or 25 to 33 weight percent, or greater than 25 and less than 33 weight percent, based on the total weight of the conductive layer equaling 100 weight percent. In some embodiments, the combined weight percent of the nickel and chromium in the conductive layer can be in the range of 25 to less than 32 weight percent, or 26 to 31 weight percent, or 26 to 30.5 weight percent, or 28 to 32 weight percent, or 38 to 49 weight percent, or 42 to 47 weight percent, based on the total weight of the conductive layer equaling 100 weight percent. In some embodiments, the combined weight percent of the nickel and chromium in the conductive layer can be in the range of 25 to less than 33 weight percent, or 26 to 32 weight percent, based on the total weight of the conductive layer equaling 100 weight percent.

In this fifth aspect, in addition to nickel and chromium, the conductive layer can also comprise iron wherein the weight percent of the iron in the conductive layer can be in the range of at least 35 weight percent, or at least 44 weight percent, or at least 60 weight percent to less than 75 weight percent, or greater than 60 weight percent to less than 75 weight percent, or greater than 61 weight percent to less than 75 weight percent, or greater than 61 weight percent to 74 weight percent, based on the total weight of the conductive layer equaling 100 weight percent. In some embodiments, the weight percent of the iron in the conductive layer is in the range of 61 to 75, or 65 to 75, or greater than 65 to less than 75, or 66 to less than 75, or greater than 66 to 74. In some embodiments, the weight percent of the iron in the conductive layer is 60 to 73 weight percent, greater than 60 to less than 73 weight percent, or greater than 61 weight percent to less than 73 weight percent, or greater than 61.5 weight percent up to 72 weight percent, or about 61.85 to about 72 weight percent, based on the total weight of the conductive layer equaling 100 weight percent. In some embodiments, the weight percent of the iron in the conductive layer is 44 to 73 weight percent, or 44 to 50 weight percent, or 44 to 48 weight percent, or 44 to 46 weight percent, based on the total weight of the conductive layer equaling 100 weight percent.

In embodiments of the fifth aspect, the conductive layer can comprise nickel in the range of 7 to 15 weight percent, or greater than 7 and less than 15 weight percent, or 8 to 14 weight percent, and chromium in the range of 15 to 21 weight percent, or greater than 15 to less than 21 weight percent, or 16 to 20 weight percent, and wherein the total combined weight percent of the nickel and chromium in the conductive layer is in the range of 25 to 33 weight percent, or greater than 25 and less than 33 weight percent, or 26 to 32 weight percent, based on the total weight of the conductive layer equaling 100 weight percent.

In further embodiments of the fifth aspect, the conductive layer can comprise nickel in the range of 8 to 11, or 8 to 10.5 weight percent, chromium in the range of about 18 to about 20 weight percent, and iron in the range of about 66 to about 74 weight percent and wherein the total combined weight percent of the nickel and chromium in the conductive layer is in the range of about 26 to about 31 weight percent, or 26 to 30.5 weight percent, based on the total weight of the conductive layer equaling 100 weight percent.

In certain embodiments of the fifth aspect, the conductive layer can comprise nickel in the range of 10 to 14 weight percent, chromium in the range of 16 to 18 weight percent, and iron in the range of 61 to 72, weight percent, based on the total weight of the conductive layer equaling 100 weight percent.

In certain embodiments of the fifth aspect, the conductive layer can comprise nickel in the range of 8 to 10.5 weight percent, chromium in the range of 18 to 20 weight percent, and iron in the range of 66 to 74, weight percent, based on the total weight of the conductive layer equaling 100 weight percent, and wherein the conductive layer does not include any other element species that is present in an amount greater than 2 weight percent, based on the total weight of the conductive layer equaling 100 weight percent. In one embodiment, the conductive layer further comprises manganese in the range of 0.01 to 2.0 weight percent and silicon in the range of 0.01 to 1.0 weight percent, and does not include any other element species that is present in an amount greater than 0.2, or 0.1, weight percent, based on the total weight of the conductive layer equaling 100 weight percent.

In certain embodiments of the fifth aspect, the conductive layer can comprise nickel in the range of 8 to 10.5 weight percent, chromium in the range of 18 to 20 weight percent, and iron in the range of 66 to 74, weight percent, based on the total weight of the conductive layer equaling 100 weight percent, and wherein the conductive layer further comprises manganese in the range of 0.01 to 2.0 weight percent, silicon in the range of 0.01 to 1.0 weight percent, and further comprises carbon, sulfur and phosphorous each in an amount less than 0.1 weight percent, based on the total weight of the conductive layer equaling 100 weight percent. In an embodiment, the conductive layer contains none or is substantially free of the following element species: molybdenum, niobium, cobalt, aluminum, titanium, copper or boron, or, if any species is present, such species is in an amount of less than 0.25 weight percent, or less than 0.2 weight percent, or less than 0.1 weight percent, or less than 0.05 weight percent, or trace amounts or less. In an embodiment, the conductive layer contains none, or is substantially free, of the following element species: molybdenum, niobium, cobalt, aluminum, titanium, copper or boron.

In certain embodiments of the fifth aspect, the conductive layer can comprise nickel in the range of 10 to 14 weight percent, chromium in the range of 16 to 18 weight percent, and iron in the range of 61 to 72, weight percent, based on the total weight of the conductive layer equaling 100 weight percent, and wherein the conductive layer does not include any other element species that is present in an amount greater than 3 weight percent, based on the total weight of the conductive layer equaling 100 weight percent. In one embodiment, the conductive layer further comprises molybdenum in the range of 2 to 3 weight percent, manganese in the range of 0.01 to 2.0 weight percent and silicon in the range of 0.01 to 1.0 weight percent, and does not include any other element species that is present in an amount greater than 0.2, or 0.1, weight percent, based on the total weight of the conductive layer equaling 100 weight percent.

In certain embodiments of the fifth aspect, the conductive layer can comprise nickel in the range of 10 to 14 weight percent, chromium in the range of 16 to 18 weight percent, and iron in the range of 61 to 72, weight percent, based on the total weight of the conductive layer equaling 100 weight percent, and wherein the conductive layer further comprises molybdenum in the range of 2 to 3 weight percent, manganese in the range of 0.01 to 2.0 weight percent, silicon in the range of 0.01 to 1.0 weight percent, and further comprises carbon, sulfur and phosphorous each in an amount less than 0.1 weight percent, based on the total weight of the conductive layer equaling 100 weight percent. In an embodiment, the conductive layer contains none or is substantially free of the following element species: niobium, cobalt, aluminum, titanium, copper or boron, or, if any species is present, such species is in an amount of less than 0.25 weight percent, or less than 0.2 weight percent, or less than 0.1 weight percent, or less than 0.05 weight percent, or trace amounts or less. In an embodiment, the conductive layer contains none, or is substantially free, of the following element species: niobium, cobalt, aluminum, titanium, copper or boron.

In a sixth aspect, the conductive layer can comprise nickel in the range of 10 to 30 weight percent, or greater than 10 and less than 30 weight percent, or 11 to 29 weight percent; chromium in the range of 16 to 26 weight percent, or 17 to 26 weight percent, or greater than 17 to less than 26 weight percent, or 18 to 25 weight percent; and molybdenum in the range of 2 to 8 weight percent, or greater than 2 and less than 8 weight percent, or 2.5 to 7 weight percent, based on the total weight of the conductive layer equaling 100 weight percent.

In embodiments of the sixth aspect, the conductive layer can comprise nickel in the range of 10 to 16 weight percent, or greater than 10 and less than 16 weight percent, or 11 to 15 weight percent; chromium in the range of 17 to 21 weight percent, or greater than 17 to less than 21 weight percent, or 18 to 20 weight percent; molybdenum in the range of 2 to 5 weight percent, or greater than 2 and less than 5 weight percent, or 3 to 4 weight percent; and iron in the range of 55 to 70 weight percent, or greater than 55 to less than 70 weight percent, or 57 to 68 weight percent, based on the total weight of the conductive layer equaling 100 weight percent.

In embodiments of the sixth aspect, the conductive layer can comprise nickel in the range of 12.5 to 29 weight percent, or greater than 12.5 and less than 29 weight percent, or 13.5 to 28 weight percent; chromium in the range of 16 to 24 weight percent, or greater than 16 to less than 24 weight percent, or 17 to 23 weight percent; molybdenum in the range of 3 to 6 weight percent, or greater than 3 and less than 6 weight percent, or 4 to 5 weight percent; and iron in the range of 46 to 66 weight percent, or greater than 46 to less than 66 weight percent, or 47 to 65 weight percent, based on the total weight of the conductive layer equaling 100 weight percent.

In embodiments of the sixth aspect, the conductive layer can comprise nickel in the range of 16 to 26.5 weight percent, or greater than 16 and less than 26.5 weight percent, or 17 to 25.5 weight percent; chromium in the range of 18 to 23 weight percent, or greater than 18 to less than 23 weight percent, or 19 to 22 weight percent; molybdenum in the range of 5 to 8 weight percent, or greater than 5 and less than 8 weight percent, or 6 to 7 weight percent; and iron in the range of 41 to 62 weight percent, or greater than 41 to less than 62 weight percent, or 42 to 61 weight percent, based on the total weight of the conductive layer equaling 100 weight percent.

In embodiments of the sixth aspect, the conductive layer does not include any other element species (in addition to those specified above) that is present in an amount greater than 2 weight percent, based on the total weight of the conductive layer equaling 100 weight percent. In one embodiment, the conductive layer further comprises manganese in the range of 0.01 to 2.0 weight percent and silicon in the range of 0.01 to 1.0 weight percent, and does not include any other element species that is present in an amount greater than 0.2, or 0.1, or 0.05 weight percent, based on the total weight of the conductive layer equaling 100 weight percent.

In embodiments of the invention, the conductive layer is metal comprising or produced from one or more of the following alloys: Stainless Steel (SS) 354 SMO, SS 304, SS 316, SS 317L, SS 317LM, SS 317LMN, SS 904, SS AL-6XN, or SS Alloy 24. In embodiments of the invention, the conductive layer is metal chosen from one or more of the following alloys: Stainless Steel (SS) 354 SMO, SS 304, SS 316, SS 317L, SS 317LM, SS 317LMN, SS 904, SS AL-6XN, or SS Alloy 24.

In certain embodiments of the present disclosure, the conductive layer can be coated on the substrate, that can be comprised of at least one of any polymer described in the art and/or described herein including but not limited to polycarbonate, silicone polymers, acrylics, PET, modified PET such as PETG or PCTG, PCT, modified PCT, polyesters comprising TMCD AND CHDM, PCCD, PEN, or. Polyimide by physical vapor deposition.

In certain embodiments of the disclosure, the resistive material layer can comprise a thin film of resistive material deposited on the surface of the conductive layer. By the term "resistive material" is meant a material that is more electrically resistive than the conductive layer, allows current to flow upon application of a constant potential, and, when formed into a thin film electrode having a conductive layer and a resistive material layer on the conductive layer, increases the electrode's anodic stability and/or increases electron transfer kinetics, as determined by a Type 1 Linear Sweep Voltammetry Test, compared to a similar electrode with just the conductive layer. In certain embodiments, the resistive material layer comprises carbon.

In certain embodiments, the resistive material layer comprises carbon and a carbon-nitrogen ("C—N") species, e.g., a carbon-nitride. In certain embodiments, the resistive material layer comprises amorphous carbon. In certain embodiments, the resistive material layer is amorphous carbon and a carbon-nitrogen (C—N) species deposited by sputtering. In certain embodiments, the resistive material layer is amorphous carbon and a carbon-nitrogen (C—N) species deposited by sputtering using a carbon source and a nitrogen containing atmosphere. In certain embodiments, the resistive material layer is amorphous carbon and a C—N species deposited by sputtering using a carbon source in a nitrogen containing atmosphere in a separate sputtering step than a sputtering step used to deposit the conductive layer (i.e., there is no co-sputtering of the conductive layer, and the carbon and C—N species layer, being performed).

In certain embodiments, the resistive layer comprises amorphous carbon that is composed primarily of sp2 hybridized carbon, sp3 hybridized carbon, or combinations thereof, and at least one C—N species. In certain embodiments, an amorphous carbon layer comprising sp2 hybridized carbon, sp3 hybridized carbon, or combinations thereof can be formed using techniques/processes as suggested by: Onoprienko, A. A., Shaginyan, L. R., Role of microstructure in forming thin carbon film properties. Diamond Relat. Mater. 1994, 3, 1132-1136; Onoprienko, A., In Carbon, The Future Material for Advanced Technology Applications; Messina, G., Santangelo, S., Eds.; Springer Berlin Heidelberg, 2006; or Cho, N. H.; Krishnan, K. M.; Veirs, D. K.; Rubin, M. D.; Hopper, C. B.; Bhushan, B.; Bogy, D. B. Chemical structure and physical properties of diamond-like amorphous carbon films prepared by magnetron sputtering. J. Mater. Res. 1990, 5, 2543-2554. However, it has been found that such processes can be improved by depositing the carbon material, e.g., by magnetron sputtering, in an atmosphere containing a selected amount of nitrogen. The improvements can include increased deposition rate of the carbon containing resistive layer, improved electrochemical stability, sufficiently fast heterogeneous electron transfer kinetics, and improved mechanical properties (for the overall electrode film).

In certain embodiments of the disclosure, the resistive material layer can have a thickness in the range from 5 to 200 nm, the conductive layer can have a thickness in the range from 15 and 200 nm, and the substrate can have a thickness in the range from 25 and 500 μm. In certain embodiments, the biosensor component can also have visible light transmission of no more than 20% or no more than 15% or no more than 10% or no more than 5 or from 0.01 to 20% or from 0.01 to 15% or from 0.01 10% or from 0.01 to 5%, as measured by ASTM D1003.

In certain embodiments of the disclosure, the resistive material layer can have a thickness in the range from 5 to 200 nm, the conductive layer can have a thickness in the range from 15 and 200 nm, and the substrate can have a thickness in the range from 25 and 500 μm wherein the biosensor component has a visible light transmission of no more than 20%.

In certain embodiments of the disclosure, the resistive material layer can have a thickness in the range from 5 to 200 nm, the conductive layer can have a thickness in the range from 15 and 200 nm, and the substrate can have a thickness in the range from 25 and 500 μm wherein the biosensor component has a visible light transmission of no more than 15%.

In certain embodiments of the disclosure, the resistive material layer can have a thickness in the range from 5 to 200 nm, the conductive layer can have a thickness in the range from 15 and 200 nm, and the substrate can have a thickness in the range from 25 and 500 μm wherein the biosensor component has a visible light transmission of no more than 10%.

In certain embodiments of the disclosure, the resistive material layer can have a thickness in the range from 5 to 200 nm, the conductive layer can have a thickness in the range from 15 and 200 nm, and the substrate can have a thickness in the range from 25 and 500 μm wherein the biosensor component has a visible light transmission of no more than 5%.

In certain embodiments, the resistive material layer has a thickness in the range from 5 to 100 nm, or 5 to 50 nm, or 5 to 30 nm, or 5 to 25 nm, or 5 to 20 nm, or 5 to less than 20 nm, or 5 to 15 nm. In embodiments, the resistive material layer comprises amorphous carbon and at least one C—N species, and has a thickness in the range from 5 to 100 nm, or 5 to 50 nm, or 5 to 30 nm, or 5 to 25 nm, or 5 to 20 nm, or 5 to less than 20 nm, or 5 to 15 nm. In embodiments, the resistive material layer comprises amorphous carbon and at least one C—N species, and has a thickness in the range from 5 to 20 nm, or 5 to less than 20 nm, or 5 to 15 nm. In embodiments, the resistive material layer contains less than 10, or 5, or 4, or 3, or 2, or 1 weight percent, or is substantially free, of any oxygen containing species. In embodiments, there is no intentionally added oxygen-containing species to the resistive material layer. For example, there is no oxygen intentionally added to the sputtering atmosphere for sputtering the resistive material layer. However, it is contemplated that small amounts of oxygen may be present as impurities in the sputtering source material or the sputtering atmosphere, e.g., from air or water vapor that could not be fully removed from the sputtering atmosphere.

In one aspect, certain embodiments of the present disclosure relate to a biosensor component comprising a substrate, a conductive layer deposited on the substrate, and a resistive material layer deposited on the conductive layer, wherein the resistive material layer comprises carbon and at least one C—N species, wherein the conductive layer can comprise nickel and chromium in a combined weight in the range of 25 to less than 95 weight percent, chromium in an amount of at least 10 weight percent, nickel in an amount of at least 8 weight percent, iron in an amount of at least 2 weight percent, and molybdenum in an amount in the range from 0 to 20 weight percent, based on the total weight of the conductive layer equaling 100 weight percent, and wherein the substrate can be comprised of at least one of any polymer described in the art and/or described herein including but not limited to polycarbonate, silicone polymers, acrylics, PET, modified PET such as PETG or PCTG, PCT, PCTA, polyesters comprising TMCD AND CHDM, PCCD, PEN, or polyimide by any means known in the art, including but not limited to, physical vapor deposition. In embodiments, the resistive layer can have a thickness in the range of 5 to 100 nm, the conductive layer can have a thickness of between 15 and 200 nm, and the substrate can have a thickness of between 25 and 500 µm, such that the biosensor component has a visible light transmission of no more than 20% or no more than 15% or no more than 10% or no more than 5%.

One or more embodiments of the present disclosure can relate to an electrode for a biosensor, with the electrode comprising a substrate, a conductive layer deposited on the substrate, and a resistive material layer deposited on the conductive layer. In certain embodiments, the conductive layer can comprise nickel and chromium, and the conductive layer can have an oxidation wave voltage for Fe(II)[CN]6 mediator (identified below as Epeak,anodic) of less than 1000, or less than 950, or less than 925, or less than about 900 millivolts (mV), as determined in a Type 1 Linear Sweep Voltammetry Test (as discussed in the Examples section). In certain embodiments, the conductive layer can comprise nickel and chromium, and the conductive layer can have an oxidation wave voltage for Fe(II)[CN]6 mediator (identified below as Epeak, anodic) of less than 450, or less than 400, or less than 375, or less than 350, or less than 325, or less than 300, or less than 275 millivolts (mV), as determined in a Type 1 Linear Sweep Voltammetry Test (as discussed in the Examples section).

In one aspect, embodiments of the present disclosure can relate to an electrode for a biosensor, with the electrode comprising a substrate, a conductive layer deposited on the substrate, and a resistive material (e.g., amorphous carbon and at least one C—N species) layer deposited on the conductive layer, wherein the conductive layer can comprise nickel, chromium, and iron (as described in the various aspects and embodiments above), and wherein the electrode can have an oxidation wave voltage for Fe(II)[CN]6 mediator (identified below as Epeak, anodic) of less than 1000, or less than 950, or less than 925, or less than about 900 millivolts (mV), as determined in a Type 1 Linear Sweep Voltammetry Test (as discussed in the Examples section). In embodiments, the conductive layer can comprise nickel, chromium, and iron (as described in the various aspects and embodiments above), and wherein the electrode can have an oxidation wave voltage for Fe(II)[CN]6 mediator (identified below as Epeak, anodic) of less than 450, or less than 400, or less than 375, or less than 350, or less than 325, or less than 300, or less than 275 millivolts (mV), as determined in a Type 1 Linear Sweep Voltammetry Test (as discussed in the Examples section). In one embodiment, the conductive layer can comprise nickel in amount of at least 8 weight percent, chromium in the amount of at least 10 weight percent, wherein the combined weight percent of the nickel and chromium in the conductive layer can be in the range of 25 to 95 weight percent, and wherein the conductive layer can comprise iron in an amount in a range of at least 2 weight percent and molybdenum in an amount from 0 to 20 weight percent, based on the total weight of the conductive layer equaling 100 weight percent. In another embodiment, the conductive layer can comprise nickel in amount from 8 to 72 weight percent, chromium in the amount from 14 to 20 weight percent, wherein the combined weight percent of the nickel and chromium in the conductive layer can be in the range of 25 to 90 weight percent, and wherein the conductive layer can comprise iron in an amount in a range of at least 2 to 75 weight percent and molybdenum in an amount from 0 to 20, or 0 to 10, or 0 to 5, or 0 to 2, or 0 to 1 weight percent, based on the total weight of the conductive layer equaling 100 weight percent.

In one aspect, embodiments of the present disclosure can relate to an electrode for a biosensor, with the electrode comprising a substrate, a conductive layer deposited on the substrate, and a resistive material layer deposited on the conductive layer, wherein the conductive layer can comprise nickel, chromium, and iron, and can have an oxidation wave voltage for Fe(II)[CN]6 mediator (identified below as Epeak, anodic) of less than 400, or less than 375, or less than 350, or less than 325, or less than 300, or less than 275 millivolts (mV), as determined in a Type 1 Linear Sweep Voltammetry Test (as discussed in the Examples section), and wherein the conductive layer can comprise nickel in amount greater than 70 weight percent, chromium in the range of greater than 13 to less than 20 weight percent, wherein the combined weight percent of the nickel and chromium in the conductive layer can be in the range of 80 to less than 95 weight percent, or 81 to 94 weight percent, or 82 to 94 weight percent, or 83 to 94 weight percent, or 84 to 94 weight percent, or 85 to 94 weight percent, or 86 to 94 weight percent, and wherein the conductive layer can comprise iron in an amount in a range from greater than 5 to less than 12 weight percent, or from 6 to 11 weight percent, based on the total weight of the conductive layer equaling 100 weight percent.

In one aspect, embodiments of the present disclosure can relate to an electrode for a biosensor, with the electrode comprising a substrate, a conductive layer deposited on the substrate, and a resistive material layer deposited on the conductive layer, wherein the conductive layer can comprise nickel, chromium, and iron, and can have an oxidation wave voltage for Fe(II)[CN]6 mediator (identified below as Epeak, anodic) of less than 400, or less than 375, or less than 350, or less than 325, or less than 300, or less than 275 millivolts (mV), as determined in a Type 1 Linear Sweep Voltammetry Test (as discussed in the Examples section), and wherein the conductive layer can comprise nickel in amount from 7 to less than 15 weight percent, chromium in the range of greater than 15 to less than 22 weight percent, wherein the combined weight percent of the nickel and chromium in the conductive layer can be in the range of 25 to 33 weight percent, or 25 to less than 33 weight percent, or 26 to 32 weight percent, and wherein the conductive layer can comprise iron in an amount in a range from 60 to less than 75 weight percent, or from 61 to 74 weight percent, based on the total weight of the conductive layer equaling 100 weight percent. In one embodiment, the conductive layer can comprise nickel in amount from 8 to 11 weight percent, or 8 to less than 11 weight percent, or 8 to 10.5 weight percent, chromium in the range of 17 to 21 weight percent, or 18 to 20 weight percent, wherein the combined weight percent of the nickel and chromium in the conductive layer can be in the range of 25 to 32 weight percent, or 26 to 31 weight percent, or 26 to 30.5 weight percent, and wherein the conductive layer can comprise iron in an amount in a range from 65 to less than 75 weight percent, or from 66 to 74 weight percent, based on the total weight of the conductive layer equaling 100 weight percent. In one embodiment, the conductive layer can comprise nickel in amount from 9 to 15 weight percent, or 10 to 14 weight percent, chromium in the range of 15 to 19 weight percent, or 16 to 18 weight percent, wherein the combined weight percent of the nickel and chromium in the conductive layer can be in the range of 25 to 33 weight percent, or 26 to 32 weight percent, and wherein the conductive layer can comprise iron in an amount in a range from 60 to less than 73 weight percent, or from 61 to 72 weight percent, or from 61.5 to 72 weight percent, based on the total weight of the conductive layer equaling 100 weight percent.

The substrate can be comprised of any polymer composition known in the art including but not limited to at least one polymer selected from the groups consisting of: nylon, polyesters, copolyesters, polyethylene, polypropylene, polyamides; polystyrene, polystyrene copolymers, styrene acrylonitrile copolymers, acrylonitrile butadiene styrene copolymers, poly(methylmethacrylate), acrylic copolymers, polyimides, poly(ether-imides); polyphenylene oxides or poly(phenylene oxide)/polystyrene blends, polystyrene resins; polyphenylene sulfides; polyphenylene sulfide/sulfones; poly(ester-carbonates); polycarbonates; polysulfones; polysulfone ethers; and poly(ether-ketones); or mixtures of any of the other foregoing polymers.

In one embodiment, the substrate can be comprised of at least one polyester comprising residues of at least one glycol selected from the group consisting of ethylene glycol, 1,4-cyclohexanedimethanol, and 2,2,4,4-tetramethyl-1,3-cyclobutanediol.

In one embodiment, the substrate can be comprised of at least one polyester comprising residues of terephthalic acid and/or dimethyl terephthalate and residues of at least one glycol selected from the group consisting of ethylene glycol, 1,4-cyclohexanedimethanol, and 2,2,4,4-tetramethyl-1,3-cyclobutanediol.

In one embodiment, the substrate can be comprised of at least one polyester comprising an acid component which comprises residues of terephthalic acid and isophthalic acid and/or esters thereof such as dimethyl terephthalate, and at glycol component comprising residues of at least one glycol selected from the group consisting of ethylene glycol residues, 1,4-cyclohexanedimethanol residues, and 2,2,4,4-tetramethyl-1,3-cyclobutanediol.

In one embodiment, the substrate can be comprised of at least one polyester comprising terephthalic acid residues, or an ester thereof, or mixtures thereof, and 1,4-cyclohexanedimethanol residues.

In one embodiment, the substrate can be comprised of at least one polyester made from terephthalic acid residues, or an ester thereof, or mixtures thereof, and 1,4-cyclohexanedimethanol residues and/or 2,2,4,4-tetramethyl-1,3-cyclobutanediol residues.

In one embodiment, the substrate can be comprised of at least one polyester made from terephthalic acid residues, or an ester thereof, or mixtures thereof, 2,2,4,4-tetramethyl-1,3-cyclobutanediol residues, and 1,4-cyclohexanedimethanol residues.

In one embodiment, the substrate can be comprised of at least one polyester made from terephthalic acid residues, or an ester thereof, or mixtures thereof, 2,2,4,4-tetramethyl-1,3-cyclobutanediol residues, and ethylene glycol residues.

In one embodiment, the substrate can be comprised of at least one polyester comprising terephthalic acid residues, or an ester thereof, or mixtures thereof, ethylene glycol residues, and 1,4-cyclohexanedimethanol residues.

Conductive layers in the present disclosure can be constructed of a single layer comprising any of the alloy compositions disclosed in this application. In certain embodiments, the alloy composition contains an alloy which can be a solid solution of the elements (a single phase), a mixture of metallic phases (two or more solutions) or an intermetallic compound with no distinct boundary between the phases.

One or more embodiments of the present disclosure concern a method for forming an electrode, e.g., for a biosensor. The method comprises (a) providing a substrate; (b) providing a conductive layer target; (c) forming a conductive layer by physical vapor deposition of at least a portion of the substrate with material from the conductive layer target to thereby form a conductive layer on the substrate having a conductive layer surface facing opposite the substrate; (d) providing a target that when used as the source material for physical vapor deposition, produces a resistive material hereafter referred to as "resistive material target"; (e) providing an atmosphere containing nitrogen for the resistive material target and conductive layer surface; and (f) forming a resistive material layer by physical vapor deposition of at least a portion of the conductive layer (surface) with material from the resistive material target in the nitrogen-containing atmosphere to thereby form a resistive material layer on the conductive layer surface. For clarity, it should be understood that the resistive material target can have a different composition and/or structure than the deposited resistive material. In embodiments of the invention, the atmosphere for depositing the resistive material layer contains a mixture of at least one noble gas (e.g., Ar) and nitrogen. In embodiments of the invention, nitrogen may comprise from about 0.5 to about 50%, between 1 and 50%, between 5 and 50%, between 10 and 50%, between 20 and 50%, between 10 and 45%, between 10 and 40%, or between 20 and 40% of the atmosphere (for resistive material deposition) by partial pressure.

In certain embodiments of the invention, the atmosphere for depositing the resistive material layer contains at least one noble gas (e.g., Ar) and no other intentionally added gases. However, it is contemplated that small amounts of oxygen or other elements may be present as impurities in the sputtering source material or the depositing (e.g., sputtering) atmosphere, e.g., from air or water vapor that could not be fully removed from the sputtering atmosphere.

In some embodiments of the method, the conductive material can comprise nickel in the range of at least 8 weight percent, chromium in the range of greater than 10 weight percent and iron in the range of at least 2 weight percent, wherein the total combined weight percent of the nickel and chromium in the conductive layer is in the range of 25 to less than 95 weight percent, or 25 to 90 weight percent, or 26 to 89 weight percent, based on the total weight of the conductive layer equaling 100 weight percent. In one embodiment, the conductive material can comprise molybdenum in the range from 0 to 20 weight percent, based on the total weight of the conductive layer equaling 100 weight percent. The resistive material layer can comprise amorphous carbon and at least one C—N containing species, and can have a thickness in the range from 5 to 100 nm, or 5 to 50 nm, or 5 to 25 nm, or 5 to less than 20 nm. Additionally, the combined conductive layer and resistive material layer can have a sheet resistance of less than 2000 ohms per square.

In some embodiments of the method, the conductive material can comprise nickel in the range of 8 to 72 weight percent, chromium in the range of 14 to 20 weight percent and iron in the range of greater than 5 to 75 weight percent, wherein the total combined weight percent of the nickel and chromium in the conductive layer is in the range of 25 to less than 95 weight percent, or 25 to 90 weight percent, or 26 to 89 weight percent, based on the total weight of the conductive layer equaling 100 weight percent. The resistive material layer can comprise amorphous carbon and at least one C—N species, and have a thickness in the range from 5 to 100 nm, or 5 to 50 nm, or 5 to 25 nm, or 5 to less than 20 nm. Additionally, the combined conductive layer and resistive material layer can have a sheet resistance of less than 2000 ohms per square. In addition to nickel, chromium and iron, the conductive layer can also comprise up to 2 weight percent manganese and up to 1 weight percent silicon, based on the total weight of the conductive layer equaling 100 weight percent.

In some embodiments of the method, the conductive material can comprise nickel and chromium wherein the combined weight percent of the nickel and chromium in the conductive layer can be in the range of 80 to less than 95 weight percent, or 81 to 94 weight percent, or 82 to 94 weight percent, or 83 to 94 weight percent, or 85 to 94 weight percent, or 86 to 94 weight percent, based on the total weight of the conductive layer equaling 100 weight percent. In addition to nickel and chromium, the conductive layer can also comprise iron wherein the weight percent of the iron in the conductive layer can be in the range of greater than 5 weight percent to less than 12 weight percent, or about 6 to about 11 weight percent, or 6 to 11 weight percent, or 6 to 10 weight percent, or 6 to 9 weight percent, or 7 to 10 weight percent, or 7 to 9 weight percent, or about 9 weight percent, based on the total weight of the conductive layer equaling 100 weight percent. The resistive material layer can comprise amorphous carbon and at least one C—N species, and have a thickness in the range from 5 to 100 nm, or 5 to 50 nm, or 5 to 25 nm, or 5 to less than 20 nm. Additionally, the combined conductive layer and resistive material layer can have a sheet resistance of less than 2000 ohms per square.

In some embodiments of the method, the conductive material can comprise nickel and chromium wherein the combined weight percent of the nickel and chromium in the conductive layer can be in the range of 25 to 33 weight percent, or 25 to less than 33 weight percent, or 26 to 32 weight percent, based on the total weight of the conductive layer equaling 100 weight percent. In addition to nickel and chromium, the conductive layer can also comprise iron wherein the weight percent of the iron in the conductive layer can be in the range of 60 weight percent to less than 75 weight percent, or about 61 to about 74 weight percent, or greater than 61 up to 74 weight percent, based on the total weight of the conductive layer equaling 100 weight percent. The resistive material layer can comprise amorphous carbon and at least one C—N species, and have a thickness in the range from 5 to 100 nm, or 5 to 50 nm, or 5 to 25 nm, or 5 to less than 20 nm. Additionally, the combined conductive layer and resistive material layer can have a sheet resistance of less than 2000 ohms per square.

In some embodiments of the method, the conductive material can comprise nickel in the range of 10 to 30 weight percent, or greater than 10 and less than 30 weight percent, or 11 to 29 weight percent; chromium in the range of 17 to 26 weight percent, or greater than 17 to less than 26 weight percent, or 18 to 25 weight percent; and molybdenum in the range of 2 to 8 weight percent, or greater than 2 and less than 8 weight percent, or 2.5 to 7 weight percent, based on the total weight of the conductive layer equaling 100 weight percent.

In some embodiments of the method, the conductive material can comprise nickel in the range of 10 to 16 weight percent, or greater than 10 and less than 16 weight percent, or 11 to 15 weight percent; chromium in the range of 17 to 21 weight percent, or greater than 17 to less than 21 weight percent, or 18 to 20 weight percent; molybdenum in the range of 2 to 5 weight percent, or greater than 2 and less than 5 weight percent, or 3 to 4 weight percent; and iron in the range of 55 to 70 weight percent, or greater than 55 to less than 70 weight percent, or 57 to 68 weight percent, based on the total weight of the conductive layer equaling 100 weight percent.

In some embodiments of the method, the conductive material can comprise nickel in the range of 12.5 to 29 weight percent, or greater than 12.5 and less than 29 weight percent, or 13.5 to 28 weight percent; chromium in the range of 16 to 24 weight percent, or greater than 16 to less than 24 weight percent, or 17 to 23 weight percent; molybdenum in the range of 3 to 6 weight percent, or greater than 3 and less than 6 weight percent, or 4 to 5 weight percent; and iron in the range of 46 to 66 weight percent, or greater than 46 to less than 66 weight percent, or 47 to 65 weight percent, based on the total weight of the conductive layer equaling 100 weight percent.

In some embodiments of the method, the conductive material can comprise nickel in the range of 16 to 26.5 weight percent, or greater than 16 and less than 26.5 weight percent, or 17 to 25.5 weight percent; chromium in the range of 18 to 23 weight percent, or greater than 18 to less than 23 weight percent, or 19 to 22 weight percent; molybdenum in the range of 5 to 8 weight percent, or greater than 5 and less than 8 weight percent, or 6 to 7 weight percent; and iron in the range of 41 to 62 weight percent, or greater than 41 to less than 62 weight percent, or 42 to 61 weight percent, based on the total weight of the conductive layer equaling 100 weight percent.

In some embodiments of the method, the conductive material does not include any other element species (in addition to those specified above) that is present in an amount greater than 2 weight percent, based on the total weight of the conductive layer equaling 100 weight percent. In one embodiment, the conductive material further comprises manganese in the range of 0.01 to 2.0 weight percent and silicon in the range of 0.01 to 1.0 weight percent, and does not include any other element species that is present in an amount greater than 0.2, or 0.1, or 0.05 weight percent, based on the total weight of the conductive layer equaling 100 weight percent.

In some embodiments of the method, the conductive material is metal comprising or produced from one or more of the following alloys: Stainless Steel (SS) 354 SMO, SS 304, SS 316, SS 317L, SS 317LM, SS 317LMN, SS 904, SS AL-6XN, or SS Alloy 24. In some embodiments of the method, the conductive material is metal chosen from one or more of the following alloys: Stainless Steel (SS) 354 SMO, SS 304, SS 316, SS 317L, SS 317LM, SS 317LMN, SS 904, SS AL-6XN, or SS Alloy 24.

One or more embodiments of the present disclosure concern a method for forming an electrode for a biosensor. The combined conductive layer and resistive material layer can have a sheet resistance, as measured by ASTM F1711-96, of no more than 5000, 2000, 100, 80, 60, 50, 40, 20, 10, or 5 ohms per square. In some embodiments, the layers can have a sheet resistance of between 1 to 5000 ohms per square, 1 to 4000 ohms per square, 1 to 3000 ohms per square, 1 to 2000 ohms per square, 1 to 1000 ohms per square, 1 to 500 ohms per square, 5 to 100 ohms per square, 5 to 20 ohms per square, 5 to 15 ohms per square, 5 to 10 ohms per square, 10 to 80 ohms per square, 20 to 60 ohms per square, or 40 to 50 ohms per square, as measured by ASTM F1711-96. The layers can have a sheet resistance of less than 2000 ohms per square.

BRIEF DESCRIPTION OF THE FIGURES

Embodiments of the present disclosure are described herein with reference to the following figures, wherein.

DETAILED DESCRIPTION

Figure 1:
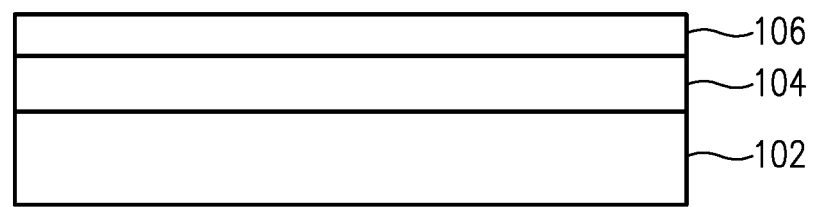
FIG. 1 is a sectional schematic illustration of a thin-film electrode biosensor component of embodiments of the present disclosure.
Figure 2:
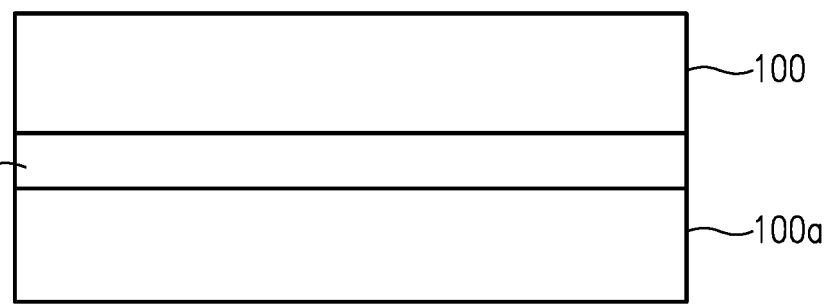
FIG. 2 is a schematic illustration of a test-strip biosensor component of embodiments of the present disclosure.

The present invention is generally directed to a component for an electrode such as those used in a biosensor. As used herein, the term "biosensor" shall denote a device for analyzing biological samples. In some embodiments, as illustrated in FIG. 1, the biosensor component may be a layered thin-film electrode 100 and may broadly comprise a substrate 102, a conductive layer 104 deposited on at least a portion of the substrate 102, and a resistive material layer 106 deposited on at least a portion of the conductive layer 104. In some embodiments, the biosensor may be a medical sensor, such as a glucose measuring system, and the biosensor component may be a test-strip for use with the biosensor. As used herein, the term "medical sensor" shall denote a biosensor used for medical monitoring and/or diagnosis. For instance, as illustrated in FIG. 2, some embodiments contemplate that the biosensor component will comprise a test-strip 110 that includes a first electrode 100 separated from a second electrode 100a by a reaction space 112. The first electrode 100 may comprise a working electrode and the second electrode 100a may comprise a reference electrode or a counter electrode or a combined reference and counter electrode. As such, a biological sample, such as a drop of blood, can be placed within the reaction space 112 and in electrical contact with the first and second electrodes 100 and 100a for analysis. It should be understood that FIG. 2 is not intended to be limiting and shows one possible embodiment for a test strip. Other embodiments for test strips can include different configurations for the electrode(s), such as, for example, a co-planar electrode configuration. As used herein, the term "blood glucose sensor" shall denote a medical sensor used to determine a concentration of glucose in blood. In addition, a bio-reactant that reacts with the biological sample, e.g., a protein, an enzyme (e.g., glucose oxidase, glucose dehydrogenase, or the like), and a mediator (e.g., ferricyanide, ruthenium complexes, osmium complexes, quinones, phenothiazines, phenoxazines, or the like) can be formed on one or both electrodes, e.g., the working electrode.

Unlike conventional physical vapor deposited biosensor components, which normally include and/or use noble metals such as palladium and/or gold, the biosensor components described herein can be formed from non-noble metals alloys, such as those including nickel and chromium. Nevertheless, biosensor components, such as thin-film electrodes, formed from the non-noble metals alloys having a resistive material layer deposited thereon, as described herein, can exhibit superior consistency and accuracy when measuring biological samples. Thus, by using biosensor components comprised of the non-noble metal alloys and a resistive material layer, as described herein, the material and manufacturing costs typically associated with the fabrication and use of biosensor components can be significantly reduced.

Embodiments of the present disclosure provide for the substrate 102 to be formed from any type of material, either flexible or rigid, which is generally non-conductive and chemically inert to the contemplated chemical reactions described herein. In certain embodiments, the substrate 102 of the biosensor component may comprise a flexible, non-conductive film, including polymers, such as a polymeric film, a polyester film, a polycarbonate film, or the like. In certain specific embodiments, the substrate 102 may comprise a polyethylene terephthalate (PET) film. Embodiments of the present disclosure contemplate that the substrate 102 may have a thickness of at least 25 μm, 125 μm, or 250 μm, and/or not more than 800 μm, 500 μm, or 400 μm. In certain embodiments, the substrate 102 may have a thickness of between 25 to 800 μm, 25 to 500 μm, or 25 to 400 μm, between 125 to 800 μm, 125 to 500 μm, or 125 to 400 μm, or between 250 to 800 μm, 250 to 500 μm, or 250 to 400 μm.

The conductive layer 104 coated on the substrate 102 may comprise one or more non-noble metals. Such conductive layer 104 may be coated on the substrate 102 via one or more physical vapor deposition techniques, such as sputter coating (e.g., magnetron sputtering, unbalanced magnetron sputtering, ion beam sputtering, facing targets sputtering, or the like), thermal evaporation, electron beam evaporation, arc vaporization, co-evaporation, ion plating, or the like, or combinations thereof. The conductive layer 104 may be coated on the substrate 102 to a thickness of at least 1, 10, 15, or 30 nm, and/or not more than 1000, 200, 100, or 50, nm. In certain embodiments, the conductive layer 104 may have a thickness of between 1 to 1000 nm, 1 to 200 nm, 1 to 100 nm, or 1 to 50 nm, between 10 to 1000 nm, 10 to 200 nm, 10 to 100 nm, or 10 to 50 nm, between 15 to 1000 nm, 15 to 200 nm, 15 to 100 nm, or 15 to 50 nm, or between 30 to 1000 nm, 30 to 200 nm, 30 to 100 nm, or 30 to 50 nm.

The resistive material layer 106 may be deposited on the conductive layer 104 via one or more physical vapor deposition techniques, such as sputter coating (e.g., magnetron sputtering, unbalanced magnetron sputtering, ion beam sputtering, facing targets sputtering, or the like), thermal evaporation, electron beam evaporation, arc vaporization, co-evaporation, ion plating, plasma enhanced vapor deposition, atomic layer deposition, or the like, or combinations thereof. In certain embodiments, the resistive material layer 106 may be coated on the substrate 104 to a thickness of at least 1, 5, 10, or 15 nm, and/or not more than 200, 100, 50, 25, 20, an amount less than 20, or 15 nm. In certain embodiments, the resistive layer 106 may have a thickness of from 1 to 200 nm, 1 to 100 nm, 1 to 50 nm, 1 to 20 nm, 1 to less than 20 nm, or 1 to 15 nm; or from 5 to 200 nm, 5 to 100 nm, 5 to 50 nm, 5 to 25 nm, 5 to 20 nm, 5 to less than 20 nm, or 5 to 15 nm; or from 10 to 200 nm, 10 to 100 nm, 10 to 50 nm, or 10 to 25 nm, 10 to 20 nm, 10 to less than 20 nm, or 10 to 15 nm.

The conductive layer 104 and resistive material layer 106 may be deposited on the substrate 102, such that the resulting thin-film electrode 100 will generally be opaque to visible light. For example, the resulting thin-film electrode 100 may have a visible light transmission, as measured by ASTM D1003, of no more than 50%, no more than 40%, no more than 30%, or no more than 20%. In certain embodiments, the resulting thin-film electrode 100 may have a visible light transmission of between 1 to 50%, between 10 to 40%, between 15 to 30%, or about 20%. Additionally, the resulting thin-film electrode 100 may have a sheet resistance, as measured by ASTM F1711-96, of no more than 5000, 2000, 100, 80, 60, 50, 40, 20, 10, or 5 ohms per square. In some embodiments, the resulting thin-film electrode 100 may have a sheet resistance of between 1 to 5000 ohms per square, 2 to 2000 ohms per square, 5 to 100 ohms per square, 10 to 80 ohms per square, 20 to 60 ohms per square, or 40 to 50 ohms per square.

Non-noble metals described herein, which form a conductive layer 104, may be comprised of alloys of nickel and chromium. For example, non-noble metal alloys comprised of at least 4, or 5, or 6, or 8 weight percent nickel and at least 10 weight percent chromium were used to prepare conductive layers 104 of a biosensor component, wherein the conductive layers were further coated by depositing a resistive material layer 106 (that includes amorphous carbon and at least one C—N species) on the conductive layer 104. Table 1 includes alloys containing nickel and chromium that were used to prepare electrodes comprising both a conductive layer and a resistive material layer. The resistive material layers that were prepared include layers that contain amorphous carbon and layers that contain both amorphous carbon and at least one C—N species. It should be understood that, unless specifically stated otherwise, weight percentages provided herein for elements contained in the conductive layer are based on the total weight of the conductive layer only, and do not include elements contained in the resistive layer.

In addition to the alloys described in Table 1, in certain embodiments, the amount of nickel and chromium included in the non-noble metal alloys that comprise the conductive layer of the electrode (for example, conductive layer 104 of the biosensor component) and the elemental amounts can vary depending on the specific requirements of the electrode, for example, the biosensor component. In various embodiments, the non-noble metal alloys can comprise at least about 4, or 5, or 6, or 8 to about 72 weight percent of nickel. Additionally, in various embodiments, the non-noble metal alloys can comprise at least about 10, 13, 14, and/or up to about 30, 25, 20, 19, 18, or 17 weight percent of chromium. More particularly, in embodiments, the non-noble metal alloys can comprise in the range of about 12 to 30, 12 to 25, 13 to 20, 13 to 19, 13 to 18, 13 to 17, 14 to 20, 14 to 19, 14 to 18, or 14 to 17 weight percent of chromium.

In various embodiments, the non-noble metal alloys can comprise at least about 5 to about 95 weight percent of nickel. Additionally, in various embodiments, the non-noble metal alloys can comprise at least about 5, 10, 20, greater than 20, 25, 30, 40, 50, or greater than 50, 60 and/or up to about 95, 90, 80, 70, 60, greater than 50, 50, or 40 weight percent of chromium. More particularly, in embodiments, the non-noble metal alloys can comprise in the range of about 5 to 95, 10 to 90, 10 to 80, 10 to 70, 10 to 60, 10 to 50, 10 to 40, 20 to 90, 20 to 80, 20 to 70, 20 to 60, 20 to 50, 20 to 40, greater than 20 to 90, greater than 20 to 80, greater than 20 to 70, greater than 20 to 60, greater than 20 to 50, greater than 20 to 40, 25 to 90, 25 to 80, 25 to 70, 25 to 60, 25 to 50, 25 to 40, 30 to 90, 30 to 80, 30 to 70, 30 to 60, 30 to 50, 30 to 40, 40 to 90, 40 to 80, 40 to 70, 40 to 60, 40 to 50, 50 to 90, 50 to 80, 50 to 70, 50 to 60, greater than 50 to 95, greater than 50 to 90, greater than 50 to 80, greater than 50 to 70, greater than 50 to 60, 60 to 95, 60 to 90, 60 to 80, 60 to 70, 70 to 95, 70 to 90, 70 to 80, 80 to 95, or 80 to 90 weight percent of chromium. In one embodiment, in addition to the amount of chromium as specified above, the balance of the alloy is nickel. It should be understood that alloys containing nickel and chromium in a combined amount of 100 weight percent of the alloy, the alloy can still contain a small amount of other elements as impurities.

In certain embodiments, the amount of nickel and chromium included in the non-noble metal alloys that comprise the conductive layer of electrode, for example, the biosensor component, can vary depending on the specific requirements of the biosensor component as follows: 10 to 95 weight % chromium and 5 to 90 weight % nickel; 10 to 90 weight % chromium and 10 to 90 weight % nickel; or 10 to 80 weight % chromium and 20 to 90 weight % nickel; or 10 to 70 weight % chromium and 30 to 90 weight % nickel; or 10 to 60 weight % chromium and 40 to 90 weight % nickel; or 10 to 50 weight % chromium and 50 to 90 weight % nickel, or 10 to 40 weight % chromium and 60 to 90 weight % nickel; or 20 to 90 weight % chromium and 10 to 80 weight % nickel; or 20 to 80 weight % chromium and 20 to 80 weight % nickel; or 20 to 70 weight % chromium and 30 to 80 weight % nickel; or 20 to 60 weight % chromium and 40 to 80 weight % nickel; or 20 to 50 weight % chromium and 50 to 80 weight % nickel; or 20 to 40 weight % chromium and 60 to 80 weight % nickel; or greater than 20 to 90 weight % chromium and 10 to less than 80 weight % nickel; or greater than 20 to 80 weight % chromium and 20 to less than 80 weight % nickel; or greater than 20 to 70 weight % chromium and 30 to less than 80 weight % nickel; or greater than 20 to 60 weight % chromium and 40 to less than 80 weight % nickel; or greater than 20 to 50 weight % chromium and 50 to less than 80 weight % nickel; or greater than 20 to 40 weight % chromium and 60 to less than 80 weight % nickel; or 25 to 90 weight % chromium and 10 to 75 weight % nickel; or 25 to 80 weight % chromium and 20 to 75 weight % nickel; or 25 to 70 weight % chromium and 30 to 75 weight % nickel; or 25 to 60 weight % chromium and 40 to 75 weight % nickel; or 25 to 50 weight % chromium and 50 to 75 weight % nickel; or 25 to 40 weight % chromium and 60 to 75 weight % nickel; or 30 to 90 weight % chromium and 10 to 70 weight % nickel; or 30 to 80 weight % chromium and 20 to 70 weight % nickel; or 30 to 70 weight % chromium and 30 to 70 weight % nickel; or 30 to 60 weight % chromium and 40 to 70 weight % nickel; or 30 to 50 weight % chromium and 50 to 70 weight % nickel; or 30 to 40 weight % chromium and 60 to 70 weight % nickel; or 40 to 90 weight % chromium and 10 to 60 weight % nickel; or 40 to 80 weight % chromium and 20 to 60 weight % nickel; or 40 to 70 weight % chromium and 30 to 60 weight % nickel; or 40 to 60 weight % chromium and 40 to 60 weight % nickel; or 40 to 50 weight % chromium and 50 to 60 weight % nickel; or 50 to 95 weight % chromium and 5 to 50 weight % nickel; 50 to 90 weight % chromium and 10 to 50 weight % nickel; or 50 to 80 weight % chromium and 20 to 50 weight % nickel; or 50 to 70 weight % chromium and 30 to 50 weight % nickel; or 50 to 60 weight % chromium and 40 to 50 weight % nickel; or greater than 50 to 95 weight % chromium and 5 to less than 50 weight % nickel; or greater than 50 to 90 weight % chromium and 10 to less than 50 weight % nickel; or greater than 50 to 80 weight % chromium and 20 to less than 50 weight % nickel; or greater than 50 to 70 weight % chromium and 30 to less than 50 weight % nickel; or greater than 50 to 60 weight % chromium and 40 to less than 50 weight % nickel; or 60 to 95 weight % chromium and 5 to 40 weight % nickel; or 60 to 90 weight % chromium and 10 to 40 weight % nickel; or 60 to 80 weight % chromium and 20 to 40 weight % nickel; or 60 to 70 weight % chromium and 30 to 40 weight % nickel; or 70 to 95 weight % chromium and 5 to 30 weight % nickel; or 70 to 90 weight % chromium and 10 to 30 weight % nickel; or 70 to 80 weight % chromium and 20 to 30 weight % nickel; or 80 to 95 weight % chromium and 5 to 20 weight % nickel; or 80 to 90 weight % chromium and 10 to 20 weight % nickel; all of these weight percentages being based on the total weight percentages of the conductive layer equaling 100 weight percent.

In certain embodiments, the conductive layer contains molybdenum, if present, in an amount of 0 to 2, or 0 to 1 weight percent, based on the total weight of the conductive layer. In certain embodiments, the conductive layer contains molybdenum, if present, in an amount less than 1, or less than 0.8, or less than 0.6, or less than 0.4, or less than 0.2, or less than 0.1 weight percent, based on the total weight of the conductive layer. In embodiments, the conductive layer is substantially free of molybdenum. In embodiments, the conductive layer contains no molybdenum.

In certain embodiments, the conductive layer contains less than 1.0, or less than 0.5, or less than 0.2 weight percent of each of the following element species: iron, carbon, sulfur, phosphorous, molybdenum, niobium, cobalt, aluminum, titanium, or boron. In an embodiment, the conductive layer contains none, or is substantially free, of the following element species: carbon, sulfur, phosphorous, molybdenum, niobium, cobalt, aluminum, titanium, or boron. In certain embodiments, the conductive layer comprises nickel and chromium and contains less than 1.0, or less than 0.5, or less than 0.2, or less than 0.1, or less than 0.05 weight percent of any other element species. In certain embodiments, the conductive layer comprises nickel and chromium and contains less than 2.0, or less than 1.0, or less than 0.5, or less than 0.2, or less than 0.1, or less than 0.05 weight percent of a total of all other element species.

In certain embodiments, the amount of nickel and chromium included in the non-noble metal alloys that comprise the conductive layer of electrode, for example, the biosensor component, can vary depending on the specific requirements of the biosensor component as follows: 10 to 30 weight % chromium and 4 to 81 weight % nickel; 10 to 30 weight % chromium and 8 to 81 weight % nickel; or 10 to 25 weight % chromium and 8 to 81 weight % nickel; or 12 to 25 weight % chromium and 8 to 81 weight % nickel; or 13 to 23 weight % chromium and 8 to 81 weight % nickel; or 13 to 21 weight % chromium and 8 to 81 weight % nickel, or 14 to 20 weight % chromium and 8 to 81 weight % nickel; or 12 to 25 weight % chromium and 8 to 75 weight % nickel; or 13 to 23 weight % chromium and 8 to 75 weight % nickel; or 13 to 21 weight % chromium and 8 to 75 weight % nickel; or 14 to 20 weight % chromium and 8 to 75 weight % nickel; or 12 to 25 weight % chromium and 8 to 72 weight % nickel; or 13 to 23 weight % chromium and 8 to 72 weight % nickel; or 13 to 21 weight % chromium and 8 to 72 weight % nickel; or 14 to 20 weight % chromium and 8 to 72 weight % nickel. In certain embodiments, these metal alloys can also comprise at least 2 weight % iron; or 2 to 75 weight % iron, or 3 to 75 weight % iron; or 4 to 75 weight % iron; or 5 to 75 weight % iron.

In certain embodiments, the amount of nickel and chromium included in the non-noble metal alloys that comprise the conductive layer of electrode, for example, the biosensor component, can vary depending on the specific requirements of the biosensor component as follows: 12 to 25 weight % chromium and 70 to 81 weight % nickel; or 13 to 20 weight % chromium and 70 to 81 weight % nickel; or 13 to 19 weight % chromium and 70 to 81 weight % nickel; or 13 to 18 weight % chromium and 70 to 81 weight % nickel; or 13 to 17 weight % chromium and 70 to 81 weight % nickel, or 14 to 20 weight % chromium and 70 to 81 weight % nickel; or 14 to 19 weight % chromium and 70 to 81 weight % nickel; or 14 to 18 weight % chromium and 70 to 81 weight % nickel; or 14 to 17 weight % chromium and 70 to 81 weight % nickel; or 13 to 20 weight % chromium and 71 to 81 weight % nickel; or 13 to 19 weight % chromium and 71 to 81 weight % nickel; or 13 to 18 weight % chromium and 71 to 81 weight % nickel; or 13 to 17 weight % chromium and 71 to 81 weight % nickel; or 14 to 20 weight % chromium and 71 to 81 weight % nickel; or 14 to 19 weight % chromium and 71 to 81 weight % nickel; or 14 to 18 weight % chromium and 71 to 81 weight % nickel; or 14 to 17 weight % chromium and 71 to 81 weight % nickel; or 13 to 20 weight % chromium and 72 to 81 weight % nickel; or 13 to 19 weight % chromium and 72 to 81 weight % nickel; or 13 to 18 weight % chromium and 72 to 81 weight % nickel; or 13 to 17 weight % chromium and 72 to 81 weight % nickel; or 14 to 20 weight % chromium and 72 to 81 weight % nickel; or 14 to 19 weight % chromium and 72 to 81 weight % nickel; or 14 to 18 weight % chromium and 72 to 81 weight % nickel; or 14 to 17 weight % chromium and 72 to 81 weight % nickel; or 13 to 18 weight % chromium and 70 to 80 weight % nickel; or 13 to 17 weight % chromium and 70 to 80 weight % nickel; or 14 to 18 weight % chromium and 70 to 80 weight % nickel; or 14 to 17 weight % chromium and 70 to 80 weight % nickel; or 13 to 18 weight % chromium and 71 to 80 weight % nickel; or 13 to 17 weight % chromium and 71 to 80 weight % nickel; or 14 to 18 weight % chromium and 71 to 80 weight % nickel; or 14 to 17 weight % chromium and 71 to 80 weight % nickel; or 13 to 18 weight % chromium and 72 to 80 weight % nickel; or 13 to 17 weight % chromium and 72 to 80 weight % nickel; or 14 to 18 weight % chromium and 72 to 80 weight % nickel; or 14 to 17 weight % chromium and 72 to 80 weight % nickel; all of these weight percentages being based on the total weight percentages of the conductive layer equaling 100 weight percent. In certain embodiments, these metal alloys can also comprise at least 5 weight % iron; or 5 to 12 weight % iron, or 6 to 12 weight % iron; or 6 to 11 weight % iron.

In certain embodiments, the amount of nickel and chromium included in the non-noble metal alloys that comprise the conductive layer of electrode, for example, the biosensor component, can vary depending on the specific requirements of the biosensor component as follows: 14 to 22 weight % chromium and 7 to 15 weight % nickel; or 15 to 21 weight % chromium and 7 to 15 weight % nickel; or 16 to 20 weight % chromium and 7 to 15 weight % nickel; or 14 to 22 weight % chromium and 8 to 14 weight % nickel; or 15 to 21 weight % chromium and 8 to 14 weight % nickel, or 16 to 20 weight % chromium and 8 to 14 weight % nickel. In certain embodiments, these metal alloys can also comprise at least 61 weight % iron; or 61 to 75 weight % iron, or 61 to 74 weight % iron; or 61.5 to 75 weight % iron. In some embodiments, the conductive layer includes 17 to 21 weight % chromium and 7 to 11 weight % nickel; or 18 to 20 weight % chromium and 7 to 11 weight % nickel; or 17 to 21 weight % chromium and 8 to 11 weight % nickel; or 18 to 20 weight % chromium and 8 to 11 weight % nickel; or 18 to 20 weight % chromium and 8 to 10.5 weight % nickel; and, in embodiments, the conductive layer further includes 65 to 75 weight % iron, or 66 to 74 weight % iron; or greater than 66 up to 75 weight % iron. In some embodiments, the conductive layer includes 17 to 19 weight % chromium and 9 to 15 weight % nickel; or 16 to 18 weight % chromium and 9 to 15 weight % nickel; or 17 to 19 weight % chromium and 10 to 14 weight % nickel; or 16 to 18 weight % chromium and 10 to 14 weight % nickel; and, in embodiments, the conductive layer further includes 60 to 73 weight % iron, or 61 to 72 weight % iron; or greater than 61.5 up to 72 weight % iron.

The non-noble metal alloys that comprise the conductive layer of electrode, for example, the biosensor component, can also include iron. In various embodiments, the non-noble metal alloys can comprise at least about 2, 3, 4, 5, 6, or 7 and/or up to about 80, 75, or 74 weight percent of iron. In certain embodiments, the non-noble metal alloys can comprise in the range of 2 to less than 80, or about 2 to 75, 3 to 75, 4 to 75, 5 to 75, 6 to 75, 7 to 75, 2 to 74, 3 to 74, 4 to 74, 5 to 77, 6 to 74, 7 to 74 weight percent of iron, based on the total weight of the conductive layer equaling 100 weight percent. In certain embodiments, the non-noble metal alloys can comprise at least about 5, 6, or 7 and/or up to about 12, 11, 10, or 9 weight percent of iron. In certain embodiments, the non-noble metal alloys can comprise in the range of greater than 5 to less than 12, or about 6 to 11, 6 to 10, 6 to 9, 7 to 11, 7 to 10, 7 to 9, or about 9 weight percent of iron, based on the total weight of the conductive layer equaling 100 weight percent. In certain embodiments, the non-noble metal alloys can comprise at least about 60, 61, 62, 63, 64, 65 or 66 and/or up to about 80, 78, 76, 75 or 74 weight percent of iron. In certain embodiments, the non-noble metal alloys can comprise in the range of 60 to 80, or about 61 to 79, or 61 to 75, or 61 to 74, or 61 to 73, or 61 to 72, or 62 to 78, or 63 to 77, or 64 to 76, or 65 to 75, or 65 to less than 75, or 65 to 74, or 66 to less than 75, or 66 to 74 weight percent of iron, based on the total weight of the conductive layer equaling 100 weight percent.

In certain embodiments, non-noble metal alloys other than nickel, chromium and iron that can be present in the invention can include one or more of Group I as follows: manganese and copper and/or one or more of Group II as follows: carbon and silicon. Weight percentages of all metal alloys useful in this invention are based on the total weight percentages of materials in the conductive layer equaling 100 weight percent.

In certain embodiments, the conductive layer can further comprise at least about 0.001, 0.01, or 0.1, and/or up to 2.0, 1.5, 1.0, 0.9, 0.8, 0.7 or 0.6 weight percent of manganese. In certain embodiments, the non-noble metal alloys can comprise in the range of about 0.001 to 2.0, less than about 2.0, 0.001 to 1.0, 0.01 to 1.0, 0.1 to 1.0, or less than about 1.0 weight percent of manganese.

In certain embodiments, the conductive layer can further comprise at least about 0.001, 0.01, 0.1, or 0.2 and/or up to about 1.0, 0.5, 0.4, or 0.3 weight percent of copper. In certain embodiments, the non-noble metal alloys can comprise in the range of about 0.001 to 1.0, less than about 1.0, 0.001 to 0.5, 0.01 to 0.5, 0.1 to 0.5, or less than about 0.5 weight percent of copper.

In certain embodiments, the conductive layer can further comprise a maximum of 3.0, 2.5, 2.0, 1.5, 1.0, 0.5, 0.3, 0.2, 0.1, 0.05 or 0.015 weight percent of silicon. In certain embodiments, the conductive layer can comprise a maximum of 0.15 weight percent of carbon.

In certain embodiments, the conductive layer contains molybdenum, if present, in an amount of 0 to 20, 0 to 15, 0 to 13, 0 to 10, 0 to 5, 0 to 4, 0 to 3, 0 to 2.5, 0 to 2, or 0 to 1 weight percent, based on the total weight of the conductive layer. In certain embodiments, the conductive layer contains molybdenum, if present, in an amount less than 1, or less than 0.8, or less than 0.6, or less than 0.4, or less than 0.2, or less than 0.1 weight percent, based on the total weight of the conductive layer. In embodiments, the conductive layer is substantially free of molybdenum. In embodiments, the conductive layer contains no molybdenum.

In certain embodiments, the conductive layer contains 2 to 10, or 2 to 8, or 2 to 7.5, or 2 to 7.0, or 2 to 6.5, or 2.5 to 8, or 2.5 to 7.5, or 2.5 to 7.0, or 2.5 to 6.5, or 3 to 8, or 3 to 7.5, or 3 to 7.0, or 3 to 6.5, or 3.5 to 8, or 3.5 to 7.5, or 3.5 to 7.0, or 3.5 to 6.5, or 4 to 8, or 4 to 7.5, or 4 to 7.0, or 4 to 6.5, or 4.5 to 8, or 4.5 to 7.5, or 4.5 to 7.0, or 4.5 to 6.5, weight percent molybdenum. In certain embodiments, the conductive layer contains 2 to 6.5, or 2 to 6.0, or 2 to 5.5, or 2 to 5, or 2 to 4.5, or 2 to 4, or 2.5 to 6.5, or 2.5 to 6.0, or 2.5 to 5.5, or 2.5 to 5, or 2.5 to 4.5, or 2.5 to 4, or 3 to 6.5, or 3 to 6.0, or 3 to 5.5, or 3 to 5, or 3 to 4.5, or 3 to 4, or 3.5 to 6.5, or 3.5 to 6.0, or 3.5 to 5.5, or 3.5 to 5, or 3.5 to 4.5, or 4 to 6.5, or 4 to 6.0, or 4 to 5.5, or 4 to 5, or 4.5 to 6, or 4.5 to 5.5, or 5 to 6, weight percent molybdenum.

In certain embodiments, the conductive layer contains less than 0.2 weight percent of each of the following element species: carbon, sulfur, phosphorous, niobium, cobalt, aluminum, titanium, or boron. In an embodiment, the conductive layer contains none, or is substantially free, of the following element species: niobium, cobalt, aluminum, titanium, or boron. In an embodiment, the conductive layer contains none of the following element species: niobium, cobalt, aluminum, titanium, or boron. In an embodiment, the conductive layer contains less than 0.2 weight percent of each of the following element species: carbon, sulfur, phosphorous, molybdenum, niobium, cobalt, aluminum, titanium, or boron. In an embodiment, the conductive layer contains none, or is substantially free, of the following element species: molybdenum, niobium, cobalt, aluminum, titanium, or boron. In an embodiment, the conductive layer contains none of the following element species: molybdenum, niobium, cobalt, aluminum, titanium, or boron.

In an embodiment, the conductive layer contains none or is substantially free of the following element species: molybdenum, niobium, cobalt, aluminum, titanium, phosphorus, or boron, or, in embodiments where any species is present, such species is in an amount of less than 0.25 weight percent, or less than 0.2 weight percent, or less than 0.1 weight percent, or less than 0.05 weight percent, or trace amounts or less. In certain embodiments, the conductive layer contains none or is substantially free of the following element species: molybdenum, niobium, cobalt, aluminum, titanium, phosphorus, or boron. In an embodiment, the conductive layer contains none or is substantially free of the following element species: molybdenum, copper, niobium, cobalt, aluminum, titanium, or boron, or, in embodiments where any species is present, such species is in an amount of less than 0.25 weight percent, or less than 0.2 weight percent, or less than 0.1 weight percent, or less than 0.05 weight percent, or trace amounts or less. In certain embodiments, the conductive layer contains none or is substantially free of the following element species: molybdenum, copper, niobium, cobalt, aluminum, titanium, or boron.

In certain embodiments, the amount of nickel, chromium and iron included in the non-noble metal alloys that comprise the conductive layer of electrode, for example, the biosensor component, can vary depending on the specific requirements of the biosensor component as follows: 10 to 30 weight % chromium, 8 to 75 weight % nickel and 2 to 75 weight % iron; or 10 to 25 weight % chromium, 8 to 75 weight % nickel and 3 to 75 weight % iron; or 10 to 25 weight % chromium, 8 to 75 weight % nickel and 4 to 75 weight % iron; or 10 to 25 weight % chromium, 8 to 75 weight % nickel and 5 to 75 weight % iron; or 13 to 21 weight % chromium, 8 to 73 weight % nickel and 6 to 75 weight % iron, or 14 to 20 weight % chromium, 8 to 72 weight % nickel and 6 to 74 weight % iron, all of these weight percentages being based on the total weight percentages of the conductive layer equaling 100 weight percent.

In certain embodiments, the amount of nickel, chromium and iron included in the non-noble metal alloys that comprise the conductive layer of electrode, for example, the biosensor component, can vary depending on the specific requirements of the biosensor component as follows: 13 to 25 weight % chromium, 70 to 81 weight % nickel and greater than 5 to less than 12 weight % iron; or 13 to 20 weight % chromium, 70 to 81 weight % nickel and 6 to 11 weight % iron; or 13 to 18 weight % chromium, 70 to 81 weight % nickel and 6 to 11 weight % iron; or 14 to 17 weight % chromium, 70 to 81 weight % nickel and 6 to 11 weight % iron; or 13 to 18 weight % chromium, 72 to 81 weight % nickel and 6 to 11 weight % iron, or 14 to 17 weight % chromium, 72 to 81 weight % nickel and 6 to 11 weight % iron; or 14 to 17 weight % chromium, 72 to 81 weight % nickel and 6 to 10 weight % iron, all of these weight percentages being based on the total weight percentages of the conductive layer equaling 100 weight percent.

In certain embodiments, the amount of nickel, chromium and iron included in the non-noble metal alloys that comprise the conductive layer of electrode, for example, the biosensor component, can vary depending on the specific requirements of the biosensor component as follows: 14 to 22 weight % chromium, 7 to 15 weight % nickel and 60 to 75 weight % iron; or 15 to 21 weight % chromium, 7 to 15 weight % nickel and 61 to 75 weight % iron; or 16 to 20 weight % chromium, 7 to 15 weight % nickel and 61 to 75 weight % iron; or 16 to 20 weight % chromium, 8 to 14 weight % nickel and 61 to 75 weight % iron; or 16 to 20 weight % chromium, 8 to 14 weight % nickel and 61 to 74 weight % iron, or 16 to 20 weight % chromium, 8 to 14 weight % nickel and 61.5 to 74 weight % iron, all of these weight percentages being based on the total weight percentages of the conductive layer equaling 100 weight percent. In some embodiments, the conductive layer of electrode can include: 16 to 22 weight % chromium, 7 to 12 weight % nickel and 65 to 75 weight % iron; or 17 to 21 weight % chromium, 7 to 12 weight % nickel and 65 to 75 weight % iron; or 18 to 20 weight % chromium, 7 to 12 weight % nickel and 65 to 75 weight % iron; or 16 to 22 weight % chromium, 8 to 12 weight % nickel and 65 to 75 weight % iron; or 16 to 22 weight % chromium, 8 to 11 weight % nickel and 65 to 75 weight % iron, or 18 to 20 weight % chromium, 8 to 11 weight % nickel and 66 to 74 weight % iron, all of these weight percentages being based on the total weight percentages of the conductive layer equaling 100 weight percent. In some embodiments, the conductive layer of electrode can include: 14 to 20 weight % chromium, 8 to 16 weight % nickel and 60 to 74 weight % iron; or 15 to 19 weight % chromium, 8 to 16 weight % nickel and 60 to 74 weight % iron; or 16 to 18 weight % chromium, 8 to 16 weight % nickel and 60 to 74 weight % iron; or 14 to 20 weight % chromium, 9 to 15 weight % nickel and 60 to 74 weight % iron; or 14 to 20 weight % chromium, 10 to 14 weight % nickel and 60 to 74 weight % iron, or 16 to 18 weight % chromium, 10 to 14 weight % nickel and 61 to 72 weight % iron, all of these weight percentages being based on the total weight percentages of the conductive layer equaling 100 weight percent.

Conductive layers in the present disclosure can be constructed of a single layer comprising any of the alloy compositions disclosed in this application. In certain embodiments, the alloy composition contains an alloy which can be a solid solution of the elements (a single phase), a mixture of metallic phases (two or more solutions) or an intermetallic compound with no distinct boundary between the phases.

As one skilled in the art would readily appreciate, the elements of the non-noble metal alloys may comprise incidental impurities. As used herein, "incidental impurities" refer to any impurities that naturally occur in the ore used to the produce the non-noble metal alloys or that are inadvertently added during the production process. The non-noble metal alloys can comprise less than about 0.1, 0.05, or 0.001 weight percent of the incidental impurities.

The non-noble metal alloys described herein may also contain one or more additional alloying elements, which are in addition to the elements described above. However, in various embodiments, the non-noble metal alloys can be substantially free from such additional alloying elements. As used herein, the terms "practically free" and "substantially free" mean that the non-noble metal alloy comprises less than 0.001 weight percent of such additional alloying components. Furthermore, the terms "practically free" and "substantially free" may be used interchangeably.

In various embodiments, the resistive material layer comprises at least one C—N species in an amount greater than 20 atomic percent (at %), or greater than 25 atomic percent, or greater than 30 atomic percent, determined by x-ray photoelectron spectroscopy (XPS) analysis (as described in the Examples section below). In embodiments, the resistive material layer contains less than 20, or less than 15, or less than 14, or less than 13, or less than 12, or less than 11 atomic percent of C—O species, determined by XPS analysis.

In certain embodiments of the present disclosure, the biosensor components described herein can be prepared by performing the following steps:
(a) providing a substrate;
(b) providing a conductive layer target;
(c) forming a conductive layer by physical vapor deposition of at least a portion of the substrate with material from the target to thereby form a conductive layer on the substrate having a conductive layer surface facing opposite the substrate;
(d) providing a resistive material target;
(e) providing an atmosphere containing nitrogen for the resistive material target and conductive layer surface; and
(f) forming a resistive material layer by physical vapor depositing at least a portion of the conductive layer with material from the resistive material target in the nitrogen-containing atmosphere to thereby form a resistive material layer on the conductive layer surface.

The providing a substrate of step (a) may include the provision of any type of substrate material, such as PET, as was previously described. In certain embodiments, the substrate will comprise a sheet of substrate material that can be actuated within a high vacuum chamber. The sheet of substrate material may comprise a single section of material, such as a square sheet. In some other embodiments, sheet of substrate material may comprise a roll of material that is passed, via a roll-to-roll mechanism, through the high vacuum chamber, as will be described in more detail below. In other embodiments, the substrate may be held stationary or it may be rotating and/or orbiting during deposition, as will be also described below.

The providing a target of step (b) may include the provision of a physical vapor deposition target comprised of any of the non-noble metal alloys previously described. For example, in some embodiments, the physical vapor deposition targets comprising the alloys listed in Table 1 were used to make thin film conductive layers. Such alloy targets may comprise less than about 0.1, 0.05, or 0.001 weight percent of incidental impurities. In some embodiments, the physical vapor deposition target will be housed within and/or will comprise an electrode, such as a sputter cathode, during the physical vapor deposition process. In certain embodiments, the physical vapor deposition target may be a circular, having a diameter of at least 2, 4, 8, 12, 16, or 20 cm. In other embodiments, the physical vapor deposition target may be a tubular target having an inner diameter of at least 2, 4, 8, or 16 cm and an outer diameter of 20, 24, 28 or 32 cm. In still other embodiments, the physical vapor deposition target may be rectangular with dimensions of: a width of between 5 to 25 cm, a length of between 25 to 75 cm, and a thickness of between 0.3 to 5 cm. It should be understood, however, that embodiments of the present disclosure contemplate the use of other-shaped and sized targets.

The physical vapor depositing of step (c) generally includes the coating of the substrate with the material from the non-noble metal alloy target to form the conductive layer. As used herein, the term "physical vapor deposition" shall denote depositing thin-films by providing for the condensation of vaporized material onto a substrate. The physical vapor deposited coating may be performed with any type of physical vapor deposition process previously described, i.e., sputter coating, thermal evaporation, electron beam evaporation, arc vaporization, co-evaporation, ion plating, or the like. For example, in some embodiments, the physical vapor depositing step will be performed via a sputtering process, in which the substrate is coated with the conductive layer by sputtering the non-noble metal alloy target via the sputtering device. Specific examples of such a sputtering-type physical vapor depositing will be described in more detail below. The resulting substrate with the conductive layer coated thereon may be used as a biosensor component, such as an electrode. Such electrodes may include a working electrode, a reference electrode, and/or a counter electrode. In certain embodiments, such as when a roll of substrate material is vacuum coated with a conductive layer, via a roll-to-roll physical vapor deposition process, the resulting thin-film sheet may be cut apart to appropriate size to form a thin-film electrode specifically sized for the biosensor component. In other embodiments, the biosensor components can be formed from the thin-film sheet by etching, such as chemical or laser etching (or ablation). In still other embodiments, the biosensor components can be formed using a patterned mask, which is laid on the substrate, and the conductive layer is physical vapor deposited thereover to form the conductive layer of a biosensor component.

The providing a target of step (d) may include the provision of a physical vapor deposition target comprised of the resistive materials previously described. For example, in some embodiments, the physical vapor deposition targets comprising carbon were used to make thin film amorphous carbon containing layers. Such resistive material targets may comprise less than about 0.1, 0.05, or 0.001 weight percent of incidental impurities. In embodiments, a target can include materials that can differ from the deposited resistive layer material but, when used as the source material for physical vapor deposition, produce the resistive material. It should be understood that the resistive material target can have a different composition and/or structure than the deposited resistive material. In some embodiments, the physical vapor deposition target will be housed within and/or will comprise an electrode, such as a sputter cathode, during the physical vapor deposition process. In certain embodiments, the physical vapor deposition target may be circular, having a diameter of at least 2, 4, 8, 12, 16, or 20 cm. In other embodiments, the physical vapor deposition target may be a tubular target having an inner diameter of at least 2, 4, 8, or 16 cm and an outer diameter of 20, 24, 28 or 32 cm. In still other embodiments, the physical vapor deposition target may be rectangular with dimensions of: a width of from 5 to 25 cm, a length of between 25 to 75 cm, and a thickness of from 0.3 to 5 cm. It should be understood, however, that embodiments of the present disclosure contemplate the use of other-shaped and sized targets.

The providing of a nitrogen-containing atmosphere of step (e) may be performed in a vacuum chamber of a physical vapor deposition apparatus (or equipment) where the chamber is initially brought to a vacuum and then filled with a noble gas and nitrogen gas mixture. In certain embodiments, nitrogen may comprise from about 0.5 to about 50%, between 1 and 50%, between 5 and 50%, between 10 and 50%, between 20 and 50%, between 10 and 45%, between 10 and 40%, or from about 20 and about 40% of the atmosphere (in the chamber) by partial pressure. In one embodiment, the gas mixture is argon and nitrogen, where the amount of nitrogen can be selected.

The physical vapor depositing of step (f) generally includes the coating of the substrate with the material from the resistive material target to form the resistive material layer. As used herein, the term "physical vapor deposition" shall denote depositing thin-films by providing for the condensation of vaporized material onto a substrate. The physical vapor deposited coating may be performed with any type of physical vapor deposition process previously described, e.g., sputter coating, thermal evaporation, electron beam evaporation, arc vaporization, co-evaporation, ion plating, or the like. For example, in some embodiments, the physical vapor depositing step will be performed via a sputtering process, in which the conductive layer (previously deposited on the substrate) is coated with the resistive material layer by sputtering the resistive material target via the sputtering device. Specific examples of such a sputtering-type physical vapor depositing will be described in more detail below. The resulting substrate with the conductive layer and resistive material layer coated thereon may be used as a biosensor component, such as an electrode. In embodiments, the "resistive material" layer is a generally distinct layer from the conductive layer, forming a laminar structure, where there is a distinct interface between the layers so that each of the resistive material layer and conductive layer are separate and distinct layers, having different compositions.

In one aspect of the invention, a method of modulating the electron transfer kinetics of a thin film electrode is provided, wherein the partial pressure of nitrogen in the nitrogen-containing atmosphere (in connection with the methods for forming an electrode described herein) is selected to tune the heterogeneous electron transfer kinetics of the electrode to achieve a desired curve profile for a linear sweep or cyclic voltammogram plot. It may be advantageous to provide an electrode with slower electron transfer kinetics for certain applications.

In certain embodiments, such as when a roll of substrate material is vacuum coated with a conductive layer, followed by vacuum coating the conductive layer surface with a resistive material layer, via roll-to-roll physical vapor deposition processes, the resulting thin-film sheet may be cut apart to appropriate size to form a thin-film electrode specifically sized for the biosensor component. Such electrodes may include a working electrode, a reference electrode, and/or a counter electrode. Electrodes may also include those for the detection of conductivity of a sample, whether or not a sample has been applied to the biosensor component, or other electrical characteristics of the sample or sample environment that is useful for a biosensor. In other embodiments, the biosensor components can be formed from the thin-film sheet by etching, such as chemical or laser etching. In still other embodiments, the biosensor components can be formed using a patterned mask, which is laid on the substrate and/or conductive layer, and the conductive layer and/or the resistive material layer is physical vapor deposited thereover to form the biosensor component.

In certain specific embodiments, the biosensor components may be created via a roll-to-roll physical vapor deposition process that includes roll-to-roll magnetron sputtering. For instance, a substrate sheet comprising a polymer film made of PET (polyethylene terepthalate) with a thickness ranging from 25 μm to 250 μm and width of 33.02 cm may be sputtered using a 77.50 cm wide web roll-to-roll magnetron sputter coater, such as a the Smartweb coater offered by Applied Materials, Inc. or the Mark 80 offered by CHA Industries, Inc. A single or a dual target configuration can be employed to deposit a conductive layer of non-noble metal alloys, such as certain alloys from Table 1. A target comprised of a non-noble metal alloy plate (such as is available from Tricor Industries Inc.) can be used. A vacuum chamber of the sputter coater can be pumped down to base pressure of at least 10-5 Torr using a diffusion and mechanical pump combination. In other embodiments a combination of a mechanical pump, a turbo pump, a cryo pump, and/or an oil diffusion pump may be used. Magnetron sputtering cathodes housing the non-noble metal alloy targets having a generally rectangular shape can be energized using 2 KW power supplies (such as offered from Advanced Energy Inc.). An argon gas flow into the vacuum chamber can be controlled (such as via a MKS model 1179A flow controller) to set a sputtering pressure between 3 to 10 mTorr for use during the sputtering process.

Thickness and sheet resistance of the sputtered conductive layer can be efficiently controlled in-situ by controlling specific process parameters. Examples of process parameters include roll-to-roll web speeds (i.e., controlling the speed of the substrate sheet as it travels through the vacuum chamber during sputtering), power supplied to the sputtering targets (i.e. a product of the applied voltage and current to the plasma formed near the target surface), gas pressure in the sputtering chamber, and the number of targets present in the chamber. For example, for sputtering of a conductive layer of a given alloy, the web speed can be set to between 0.1 to 3.5 meters per minute and sputtering power density of from 1 to 8 Watts per square cm. In embodiments, sputtered conductive layer of the alloy may be formed having a measured thickness value of about 25 nm and a sheet resistance of about 45 ohms per square. In some embodiments, it is contemplated that layer thickness can be controlled by real time measurements, e.g., optical monitoring, with feedback to the deposition process.

The resistive material layer can be deposited on top of the conductive layer via one of the deposition techniques described above. For example, in one embodiment the resistive layer can be deposited using DC magnetron sputtering from a carbon target. The thickness of the resistive material layer can be controlled by controlling specific process parameters. Examples of process parameters include roll-to-roll web speeds (i.e., controlling the speed of the substrate sheet as it travels through the vacuum chamber during sputtering), power supplied to the sputtering targets (i.e., a function of the applied voltage and current to the plasma formed near the target surface), gas pressure in the sputtering chamber, and the number of targets present in the chamber. For example, in certain embodiments, for sputtering of a resistive layer on a given alloy, the web speed can be set to from 0.1 to 3.5 meters per minute and sputtering power density of from 1 to 8 Watts per square cm. In embodiments, the sputtered resistive layer may be formed having a measured thickness value of about 1-200 nm. It has also been found that the thickness and deposition rate of the carbon-containing resistive material can be altered by adjusting the partial pressure of nitrogen in the nitrogen-containing atmosphere of the vacuum chamber.

In embodiments of the invention, the atmosphere for depositing the resistive material layer contains a mixture of at least one noble gas (e.g., Ar) and nitrogen gas. In embodiments of the invention, nitrogen may comprise from about 0.5 to about 50%, between 1 and 50%, between 5 and 50%, between 10 and 50%, between 20 and 50%, between 10 and 45%, from about 10 to about 40%, from about 20 to about 40%, between 10 and 40%, or between 20 and 40% of the atmosphere (for resistive material deposition) by partial pressure. It has been found that the deposition rate of the carbon containing resistive material increases with an increased partial pressure of nitrogen (e.g., in a mixed Ar and N2 atmosphere), but appears to reach a saturation point at about 40% N2 partial pressure where additional N2 does not continue to increase the deposition rate.

It has also been found that increasing the partial pressure of nitrogen (e.g., in a mixed Ar and N2 atmosphere) in the carbon-containing resistive material deposition step results in thin film electrodes having a reduced coefficient of friction and increased scratch resistance compared to similar conductive layer films (without a resistive material layer) or to similar films with a carbon-containing resistive material layer deposited (from the same resistive source material) in a pure Ar atmosphere.

In addition to the roll-to-roll process described above, biosensor components can be manufacture using a scaled-up version of the same geometry, using a large-scale roll-to-roll process. In such a large-scale roll-to-roll process, maximum web speeds can be 0.1 to 10 meters per minute, e.g., between 3 to 7 meters per minute, or higher than 10 meters per minute. The large-scale roll-to-roll process may provide a sputtering power density between 0.1 to 13, 2 to 10, or 5 to 8 Watts per square cm. Additionally, the number of targets can include between 2, 4, 6 or more, and the web width of the substrate sheet can be from 75 cm or larger. In embodiments of the invention, the depositing steps for the conductive layer and resistive material layer may each be performed by a sputtering system operating at a power of in the range from 1.5 to 40 kW, or 1.75 to 18 kW, or 1.75 and 9 kW, or about 2 kW. Although embodiments with specific ranges have been provided above, it should be understood that deposition is controlled by applied power and rate (deposition and web speed) is proportional to power. Thus, it is desirable to run at the highest power possible for a given material for which a stable process (heat mitigation, cathode stability, voltage and current limits of power supplies, arcing) can be established. The resulting voltage for a given applied power is dependent on the composition of the target material, i.e., determined primarily by the material's secondary electron yield. Embodiments additionally contemplate that physical vapor deposition processes can be utilized in which substrate sheets batchwise are orbiting and/or rotating motion within the vacuum chamber. Certain of such embodiments, are described in detail below in the Examples section. In some embodiments in which the substrate sheets are deposited batchwise (e.g., in place, including, but not limited to, in orbiting and/or rotating motion), deposition times for depositing the conductive layer on the substrate sheets may be 5, 10, 15, 30 minutes or more.

As previously noted above, biosensor components that include a conductive layer formed from the non-noble metal alloys and a resistive material layer formed from a carbon material (in a nitrogen-containing atmosphere), as described herein, can exhibit desirable electrochemical properties that make them particularly well suited as replacements for biosensor components that incorporate noble metals, such as palladium and/or gold. For instance, the biosensor components of embodiments of the present disclosure may comprise a thin-film electrode formed with a non-noble metal alloy conductive layer and a resistive material layer that exhibits desirable dose-response characteristics when undergoing chronoamperometry tests.

In various embodiments, the conductive layer can comprise nickel, chromium, and iron (in amounts as discussed above) and the conductive layer and resistive material layer combination can have an oxidation wave voltage for Fe(II)[CN]6 mediator (identified below as Epeak, anodic) of less than 400, or less than 390, or less than 380, or less than 375, or less than 360, or less than 350, or less than 340, or less than 330, or less than 325, or less than 320, or less than 310, or less than 300, or less than 290, or less than 280, or less than 275, or less than 270, or less than 260 millivolts (mV), as determined in a Type 1 Linear Sweep Voltammetry Test (as discussed in the Examples section).

In an embodiment of the invention, the conductive layer comprises nickel, chromium, and iron (in amounts as discussed above) and the conductive layer and resistive material layer combination can have an oxidation wave voltage for Fe(II)[CN]6 mediator (identified below as Epeak, anodic) of less than 275 millivolts (mV), as determined in a Type 1 Linear Sweep Voltammetry Test (as discussed in the Examples section).

This invention can be further illustrated by the following examples of embodiments thereof, although it will be understood that these examples are included merely for the purposes of illustration and are not intended to limit the scope of the invention unless otherwise specifically indicated.

EXAMPLES

Preparation of Thin-Film Electrodes

For each of the below-described examples (and comparative examples), biosensor components in the form of thin-film electrodes were formed by the following-described physical vapor deposition process. It is understood that thin-film electrodes can be formed, using the below process, to include a conductive layer of a plurality of different types of elements and element alloys, such as the non-noble compositions listed in Table 1. The thin film electrodes of the examples also included a carbon-containing resistive material layer, or a resistive layer that contains both carbon and at least on C—N species, that was deposited on top of the conductive layer. The process included forming thin-film electrode films as follows:

(a) metal or metal alloys were deposited on 10.16 cm×10.16 cm square PET substrate sheet using direct current ("DC") magnetron sputtering in a high vacuum chamber, with the sputtering having been performed with a Denton Vacuum Desktop Pro sputtering device;

(b) the vacuum chamber was evacuated to an initial base pressure of ~$10^{-5}$ Torr;

(c) argon gas of 10 sccm was introduced into the high vacuum chamber to create a deposition pressure of ~5 mTorr;

(d) the substrate sheets were rotated at approximately two revolutions per minute within the vacuum chamber;

(e) a 5.08 cm diameter target of the metal or metal alloys was held at a constant power of 40 Watts under the DC magnetron sputtering device for deposition time of 15 minutes to coat at least a portion of the substrate sheet with the conductive layer (to initialize the targets, the targets were held at a constant power of 40 Watts under the DC magnetron sputtering device for a 5 minute pre-sputtering time prior to the substrates being introduced into the vacuum chamber);

(f) following the deposition of the conductive layer, the vacuum chamber was evacuated to an initial base pressure of ~$10^{-5}$ Torr;

(g) argon gas or a mixture of argon and nitrogen gas (depending on the example, the amount of nitrogen was varied) of 10 sccm was introduced into the high vacuum chamber to create a deposition pressure of ~5 mTorr;

(h) a carbon-containing layer was then deposited onto the conductive layer surface. A 5.08 cm diameter target of graphite material was held at a constant power of 48

Watts under the DC magnetron sputtering device for deposition time of 1 hour to coat at least a portion of the conductive layer (deposited in step e) with a carbon-containing layer (to initialize the targets, the targets were held at a constant power of 48 Watts under the DC magnetron sputtering device for a 5 minute pre-sputtering time prior to the conductive layer coated substrate being introduced into the vacuum chamber); and (i) all depositions were carried out at room temperature (i.e., ~25 C).

Similar procedures were carried out in roll-to-roll equipment where three sputtering targets were used in differentially pumped deposition zones. In the first target zone, an Ar atmosphere was used to deposit the metal or metal alloy film. In the second and third target zones, the carbon containing layer was deposited under the specified argon/nitrogen atmosphere.

Individual thin-film electrodes, with a size of 5.08 cm×7.62 cm, were cut from the thin-film electrode films that were formed by physical vapor deposition, as provided above. Electrochemical experiments were conducted using a Gamry Instruments Reference 600 potentiostat in a three electrode configuration, with the electrochemical cell containing the thin-film electrode film positioned inside of a Gamry Instruments VistaShield Faraday Cage. Each of the thin-film electrodes was formed as a working electrode by partially masking the thin-film electrode with electroplating tape having a single 3 mm diameter aperture die-cut into it. As such, an unmasked portion formed by the die-cut aperture of the thin-film electrode provided a geometric working electrode surface area of 0.0707 square cm. Another different area of unmasked portion of the thin-film electrode served as an electrical connection point to a working electrode lead of the potentiostat. The masked portion of the thin-film electrode was placed onto a flat supporting block of non-conductive material, such as plastic. The thin-film electrode was thereafter placed into a working electrode port of a glass electrochemical cell. The exposed 3 mm diameter portion of the thin-film electrode was positioned near a center of a bottom opening of a working electrode port of the electrochemical cell. The working electrode port of the electrochemical cell was sealed with a clamp and an O-ring. The electrochemical cell also contained a reference electrode comprising a saturated calomel reference electrode and a carbon auxiliary electrode. The reference electrode and the auxiliary electrode were placed, respectively in a reference electrode port and an auxiliary electrode port. Additionally, the reference electrode and the auxiliary electrode were connected, respectively, to a reference lead and an auxiliary lead of the potentiostat. The electrochemical cell also included a gas flow port by which to deaerate and blanket test solutions with inert gas, such as nitrogen. It should be noted that nitrogen is considered an inert gas for the electrochemical cell reactions, but is not considered to be inert for the plasma reactions that take place during the deposition processes (discussed above).

Thin film electrodes were prepared from stainless steel 304 and 316 alloys, respectively, both with and without a carbon-containing resistive material layer, according to the procedures discussed above. Thin film electrodes were prepared from stainless steel 317L and AL-6XN alloys, respectively, with a carbon-containing resistive material layer, according to the procedures discussed above, but test data is not provided. Although not presented in the Experiment section herein, it is believed that other conductive layer alloys, e.g., Inconel® 600 and other Ni and Cr containing alloys, can be used to provide useful electrodes in accordance with the present invention.

The stainless steel alloy compositions are listed below in Table 1. The thin film electrodes having conductive layers as listed in Table 1 also included carbon-containing resistive layers prepared according to the procedures discussed above. Carbon resistive layer thickness was approximately 15 to 45 nm (depending on the example) as determined by TEM imaging of cross-sectioned electrodes.

TABLE 1

| Alloys (source: www.matweb.com) | | | | | | | | | |
|---|---|---|---|---|---|---|---|---|---|
| | Element (% by mass) | | | | | | | | |
| Alloy | Ni | Cr | Fe | Mo | Mn | Si | C | S | P |
| SS304 | 8-10.5 | 18-20 | 66.35-74 | | 2* | 1* | 0.08* | 0.03* | 0.045* |
| SS316 | 10-14 | 16-18 | 61.85-72 | 2-3 | 2* | 1* | 0.08* | 0.03* | 0.045* |
| SS317L | 11-15 | 18-20 | 57.9-68 | 3-4 | 2* | 1* | 0.03* | 0.03* | 0.045* |
| AL-6XN | 23.5-25.5 | 20-22 | 42.4-50.5 | 6-7 | 2* | 1* | 0.03* | 0.03* | 0.04* |

*denotes maximum concentration

Type 1 Linear Sweep Voltammetry Test Description

A Type 1 Linear Sweep Voltammetry Test can be used to test the electrochemical response of the thin-film electrodes. The Type 1 Linear Sweep Voltammetry Test comprises the following steps: 50 mL of 10 mM potassium phosphate buffer containing 145 mM sodium chloride at pH 7.1 was placed into the electrochemical cell and the electrochemical cell was sealed with stoppers. Gas inlet and outlet fittings, which were associated with the gas flow port, allowed inert gas sparging (i.e., de-aerating) of the buffer solution, via a gas flow of nitrogen, using a medium-porous filter stick. The gas flow port additionally allowed the gas flow to be switched from the filter stick to a headspace-blanketing arrangement. The gas outlet was connected to an oil bubbler to prevent back-diffusion of external gas (e.g., air) into the electrochemical cell. The buffer solution was stirred with a magnetic stirbar while simultaneously sparged with nitrogen for at least 5 minutes before switching the gas flow to a blanketing configuration. No agitation of the buffer solution from sparging or otherwise was otherwise present during the electrochemical experiments conducted via the Type 1 Linear Sweep Voltammetry Test (i.e., the solution was quiescent during electrochemical testing).

A linear sweep voltammetry test was performed on the thin-film electrode that comprised the working electrode within the electrochemical cell. The initial voltage potential for linear sweep voltammetry was 0 V versus the open circuit potential (also known as the rest potential), as measured between the working electrode and the reference electrode (i.e., the saturated calomel reference electrode), and after a rest period of at least 10 seconds prior to the voltammetric experiment, the voltage potential was swept anodically at 25 mV per second until a current of at least 50 µA was observed. For solutions that contained Fe(II)[CN]6 mediator, the mediator was present at 1 or 2 mM concentration and the linear sweep voltammetry conditions were otherwise identical to mediator-free solutions.

Figure 3:
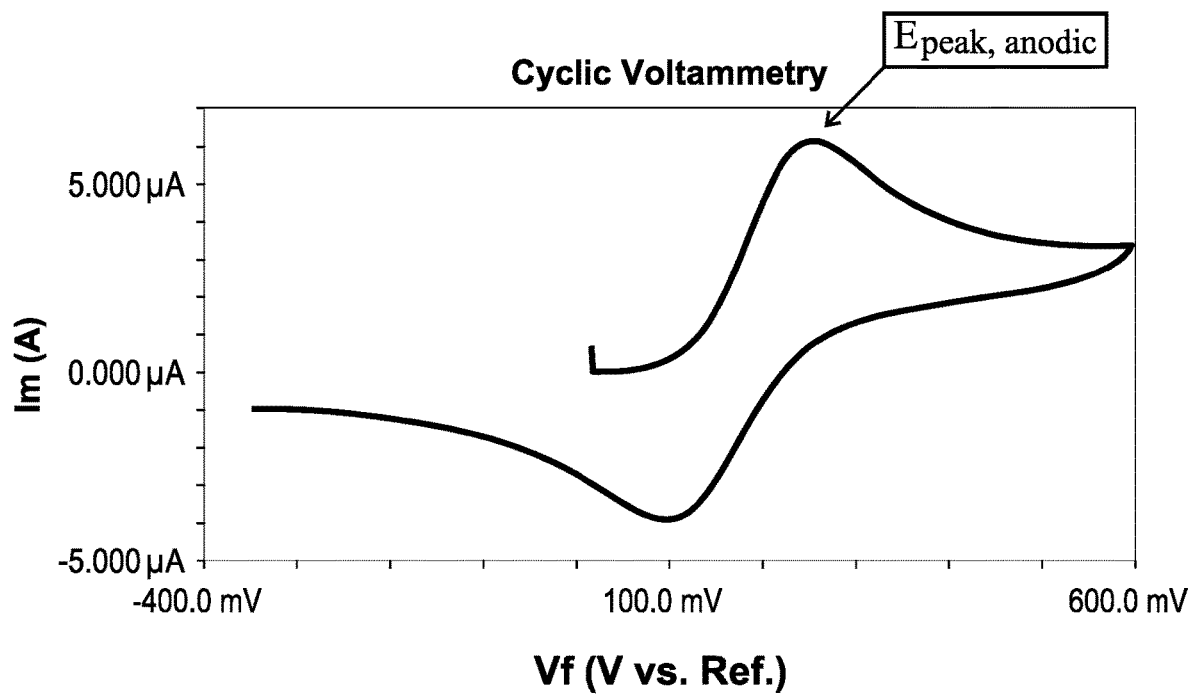
FIG. 3 is a graph depicting a cyclic sweep voltammogram plot of a thin-film electrode in a mediator-containing solution and showing the Epeak, anodic point.

A peak voltage ("Epeak,anodic") of the oxidation wave is determined, with such Epeak,anodic being defined as the voltage at which a local maximum of current is observed as a result of the oxidation of an electroactive species in solution, as measured between the working electrode and the counter electrode versus the reference electrode. An illustration of an oxidation wave and an associated $E_{peak,anodic}$, as obtained from a thin-film electrode using the Type 1 Linear Sweep Voltammetry Test, is illustrated in FIG. 3. As can be seen from FIG. 3, the measured $E_{peak,anodic}$ (or E-peak) value was approximately −76 mV, as measured versus a reference electrode.

Type 1 Cyclic Voltammetry Test Description

A Type 1 Cyclic Voltammetry Test can be used to test the electrochemical response of the thin-film electrodes. The Type 1 Cyclic Voltammetry Test comprises the following steps: 50 mL of 10 mM potassium phosphate buffer containing 145 mM sodium chloride at pH 7.1 was placed into the electrochemical cell and the electrochemical cell was sealed with stoppers. Gas inlet and outlet fittings, which were associated with the gas flow port, allowed inert gas sparging (i.e., de-aerating) of the buffer solution, via a gas flow of nitrogen, using a medium-porous filter stick. The gas flow port additionally allowed the gas flow to be switched from the filter stick to a headspace-blanketing arrangement. The gas outlet was connected to an oil bubbler to prevent back-diffusion of external gas (e.g., air) into the electrochemical cell. The solution was stirred with a magnetic stir bar while simultaneously sparged with nitrogen for at least 5 minutes before switching the gas flow to a blanketing configuration. No agitation of the buffer solution from sparging or otherwise was otherwise present during the electrochemical experiments conducted via the Type 1 Cyclic Voltammetry Test (i.e., the solution was quiescent during electrochemical testing).

A cyclic voltammetry was performed on the thin-film electrode that comprised the working electrode within the electrochemical cell. The initial voltage potential for linear sweep voltammetry was 0 V versus the open circuit potential (also known as the rest potential), as measured between the working electrode and the reference electrode (i.e., the saturated calomel reference electrode), and after a rest period of at least 10 seconds prior to the voltammetric experiment, the voltage potential was swept at a scan rate of 25 mV per second, cathodically first followed by an anodic potential sweep. For solutions that contained [RuIII(NH3)6]Cl3 mediator, the mediator was present at 1 or 2 mM concentration and the cyclic sweep voltammetry conditions were otherwise identical to mediator-free solutions.

X-Ray Photoelectron Spectroscopy (XPS)

All x-ray photoelectron spectroscopy (XPS) data was collected using a Kratos Axis Nova spectrometer. The data was processed using CasaXPS software version 2.3.17. Prior to data collection, the sample surface was cleaned in-situ with a gas cluster ion source (GCIS) using the following conditions: Mode—Argon cluster (10 keV 1000 Ar+), Raster—1 mm×1 mm, Etch time—60 s. Quantification was based on wide scan survey spectra and was reported as relative atomic mol %. All survey spectra were collected using the following conditions: X-Ray Source—Al $K_\alpha$ monochromatic source operating at 150 W (15 kV, 10 mA), Pass Energy—80 eV, Acceptance Angle—+/−15 deg. in spectroscopy mode, Take-off Angle—90 deg., Analysis area—700×300 □m, Charge neutralization—On, and Charge Correction—C 1 s 284.8 eV.

Narrow scan (high resolution) spectra were collected for the C 1 s region of the spectrum using a pass energy of 20 eV.

To determine the carbon structure, the C 1 s envelope was fit by sequential addition and subsequent fitting of synthetic peaks until a residual STD <2 was achieved. Furthermore, FWHM was restricted to <1.4 eV for peaks with a B.E. <288 eV and ≤2.0 eV for peaks with a B.E. >288 eV.

Transmission Electron Microscopy (TEM)

Narrow scan (high resolution) spectra were collected for elements of interest for peak fitting to elucidate oxidation states/chemical environments. These narrow scan spectra were collected using the same parameters described above for wide scan with the exception of pass energy. Unless otherwise specified, narrow scan spectra were collected using 20 eV pass energy. Depth profile parameters were: Mode—Argon cluster (10 kV 1000 Ar+), Raster—1 mm×1 mm, Etch time/cycle—30 s, Total number of cycles—65, and High resolution spectral data was collected for carbon, oxygen, and chromium between etches.

Film samples were cut out to approximately 2×5 mm pieces and embedded in EpoFix® cold set epoxy resin system (Electron Microscopy Sciences) under a nitrogen atmosphere for at least 12 hours. Samples were then trimmed and sectioned by ultra-microtome to produce 100 nm thick cross-sections of the film. The resulting 100 nm thick sections were transferred to a TEM grid. Samples were imaged in bright-field TEM mode using a JEOL 2100F transmission electron microscope operating at 200 keV accelerating voltage. Data were collected with a 2.5 k×4 k Gatan Orius fiber optically coupled CCD camera and processed using Gatan Digital Micrograph software.

Nano-Scratch and Coefficient of Friction Testing

Scratch testing was conducted via a progressive load scratch test using a Bruker UMT tribometer to evaluate the cohesive and adhesive properties of the various sputtered films on top of a PET substrate. All samples were scratched using a 12.5 µm diamond sphero-conical tip. The stylus was moved over the specimen surface with a linearly increasing load from 3 mN to 50 mN at the rate of 16 mN/min. The entire scratch length was 1 mm at a scratching speed of 0.33 mm/min. A small pre-scan load of 2.5 mN was applied to ensure full contact with the specimen. Normal force (Fz) and tangential force (Fx) were recorded and used to calculate coefficient of friction (COF=Fx/Fz). The failure events were examined via scanning electron microscopy (SEM). The critical load to failure is strongly related to adhesion, mechanical properties of the material, and internal stresses.

Example 1—Carbon-Containing Resistive Layer Deposition Rate

Figure 4:
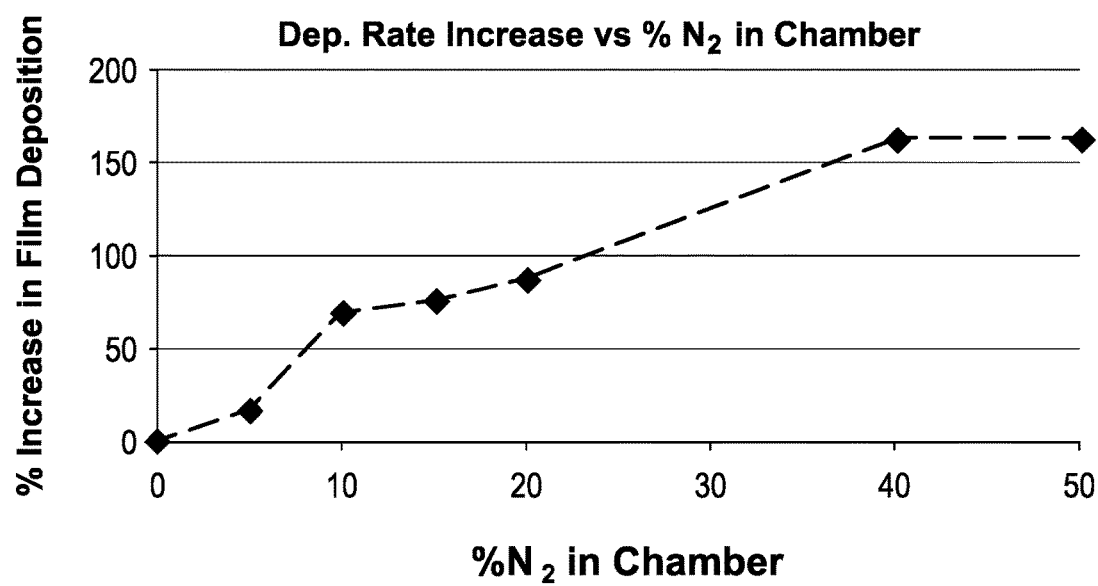
FIG. 4 is a graph showing a plot of increased deposition rate as a function of nitrogen content.

Sputter deposition rate of carbon from a graphite target was determined for various (sputtering atmosphere) N2 and Ar gas mixtures. Each thin-film sample was made in a roll-to-roll production machine, where first a SS304 layer was deposited in an amount to reach a sheet resistance of ~35 ohm/sq, followed by sputter depositing a carbon-containing layer according to the procedures for preparation of thin-film electrodes discussed above to provide the target carbon-containing layer thickness. Unexpectedly, the sheet resistance, as tested by 4-point probe, did not change with carbon deposition or thickness under any of the test conditions. The results are shown below in Table 2 and FIG. 4. A review of Table 2 and FIG. 4 reveals that the increase in carbon deposition is somewhat linear with an increase in $N_2$ concentration, up until the system reaches saturation around 40% $N_2$ (in Ar by partial pressure) where it appears the deposition rate does not continue to increase with increasing $N_2$ concentration.

TABLE 2

Deposition Rate as a Function of Nitrogen Concentration

| Sample | % N2 in Chamber | C Thickness (nm) | % Increase in C Deposition |
|---|---|---|---|
| EX 1 | 0 | 17 | — |
| EX 2 | 5 | 20 | 17 |
| EX 3 | 10 | 29 | 70 |
| EX 4 | 15 | 30 | 76 |
| EX 5 | 20 | 32 | 88 |
| EX 6 | 40 | 45 | 164 |
| EX 7 | 50 | 45 | 164 |

Example 8—Change in Discharge Voltage

Figure 5:
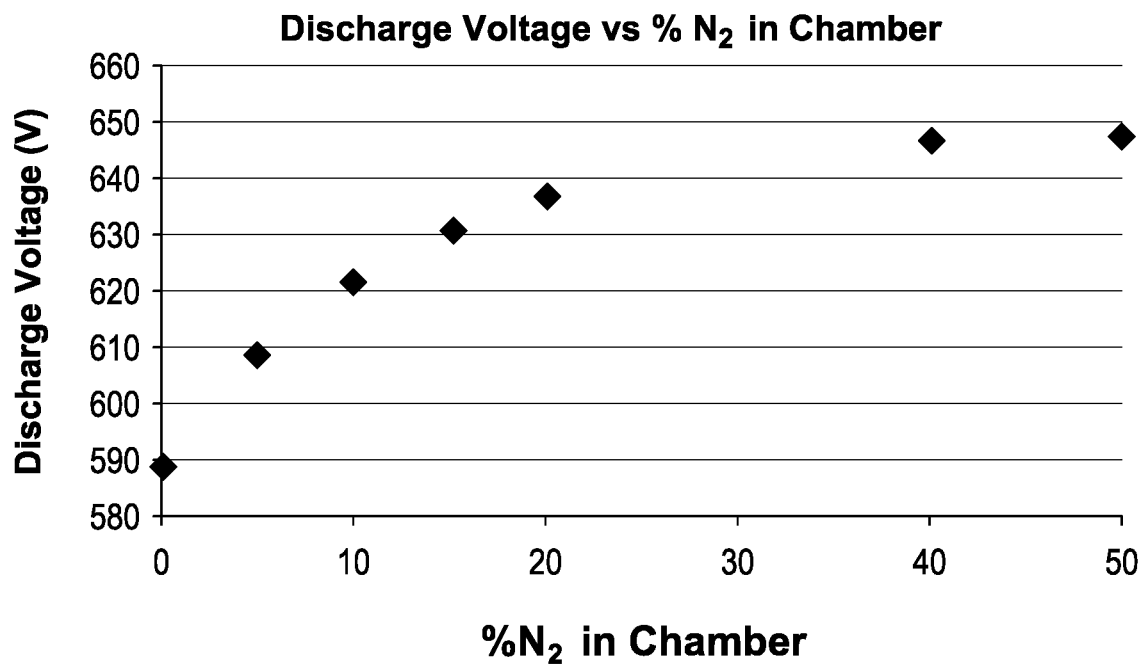
FIG. 5 is a graph showing a plot of discharge voltage as a function of nitrogen content.

The discharge voltage was determined for a graphite target for the thin-film deposition process (discussed above) as a function of $N_2$ concentration in the vacuum zone of a roll-to-roll sputtering equipment. The results are shown in FIG. 5. A review of FIG. 5 reveals that the discharge voltage increases as the $N_2$ concentration increases. It is believed that the impedance of the graphite target is increasing with increasing $N_2$ concentration and that this suggests the formation of nitrides on the surface of the graphite target.

Example 9—Characterization of Carbon-Containing Resistive Layer

Figure 6:
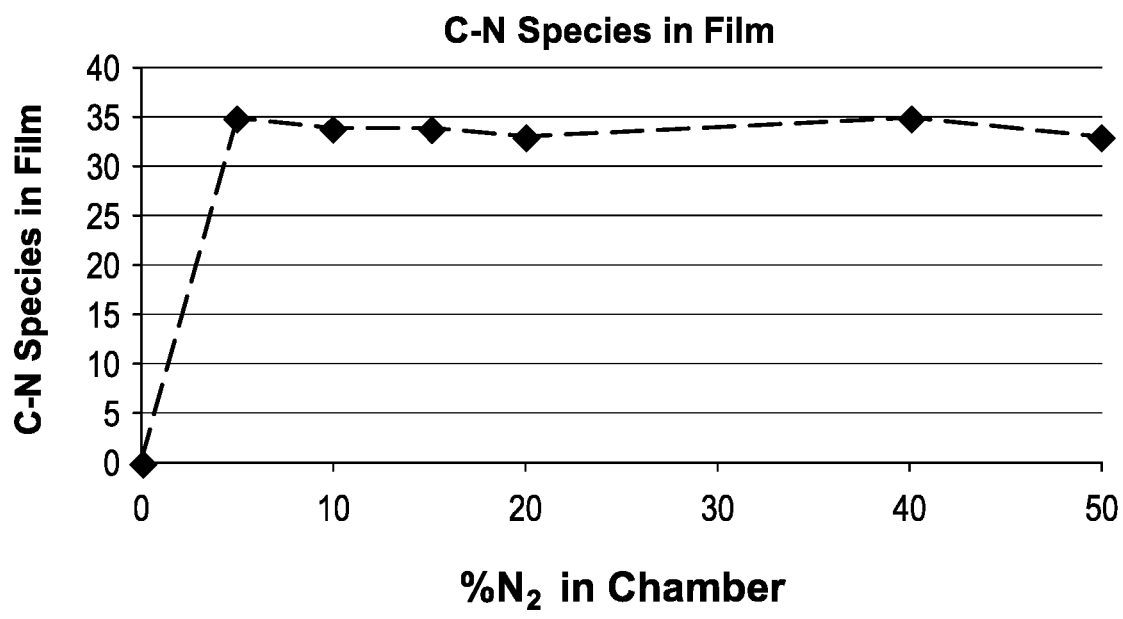
FIG. 6 is a graph showing a plot of percentage of C—N species as a function of nitrogen content.

Thin film electrodes having a conductive layer sputtered from a SS304 source and carbon-containing layers sputtered in an Ar and $N_2$ gas mixture atmosphere having various concentrations of $N_2$ were analyzed by XPS analysis to investigate the formation of a C—N species in the carbon-containing film layer as a function of nitrogen concentration in the sputtering atmosphere. All samples were sputtered on a SS304 conductive layer generated in a roll-to-roll production machine. The results are shown in FIG. 6. A review of FIG. 6 reveals that there is a rapid increase in carbon-nitride species present in the carbon-containing film, as determined by XPS analysis, and the C—N species reaches a saturation of about 35% after the nitrogen content (in the chamber) reaches about 5% by partial pressure. It was unexpected that the C—N species concentration within the sputtered film would reach saturation at such a low $N_2$ concentration. In addition, it was unexpected that these films would have similar stoichiometry because the films made with different nitrogen concentrations did have slightly different electrochemical performance and the deposition rates of carbon under these atmospheres was different, as shown in FIGS. 4 and 9-11 below.

Example 10—Carbon-Nitride Species in Resistive Layer

Figure 7:
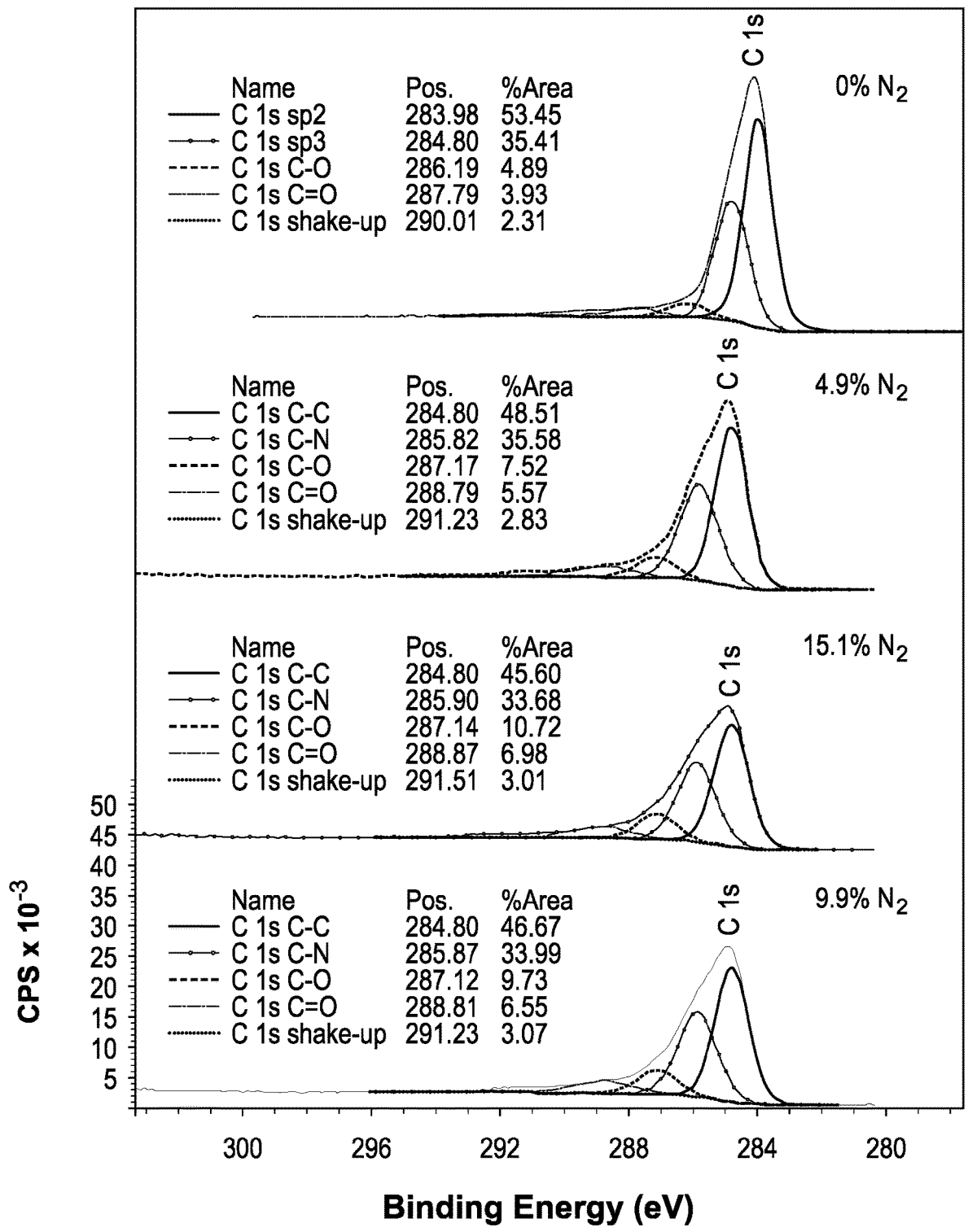
FIG. 7 is a series of plots of X-ray photoelectron spectra testing for different nitrogen content levels.
Figure 8:
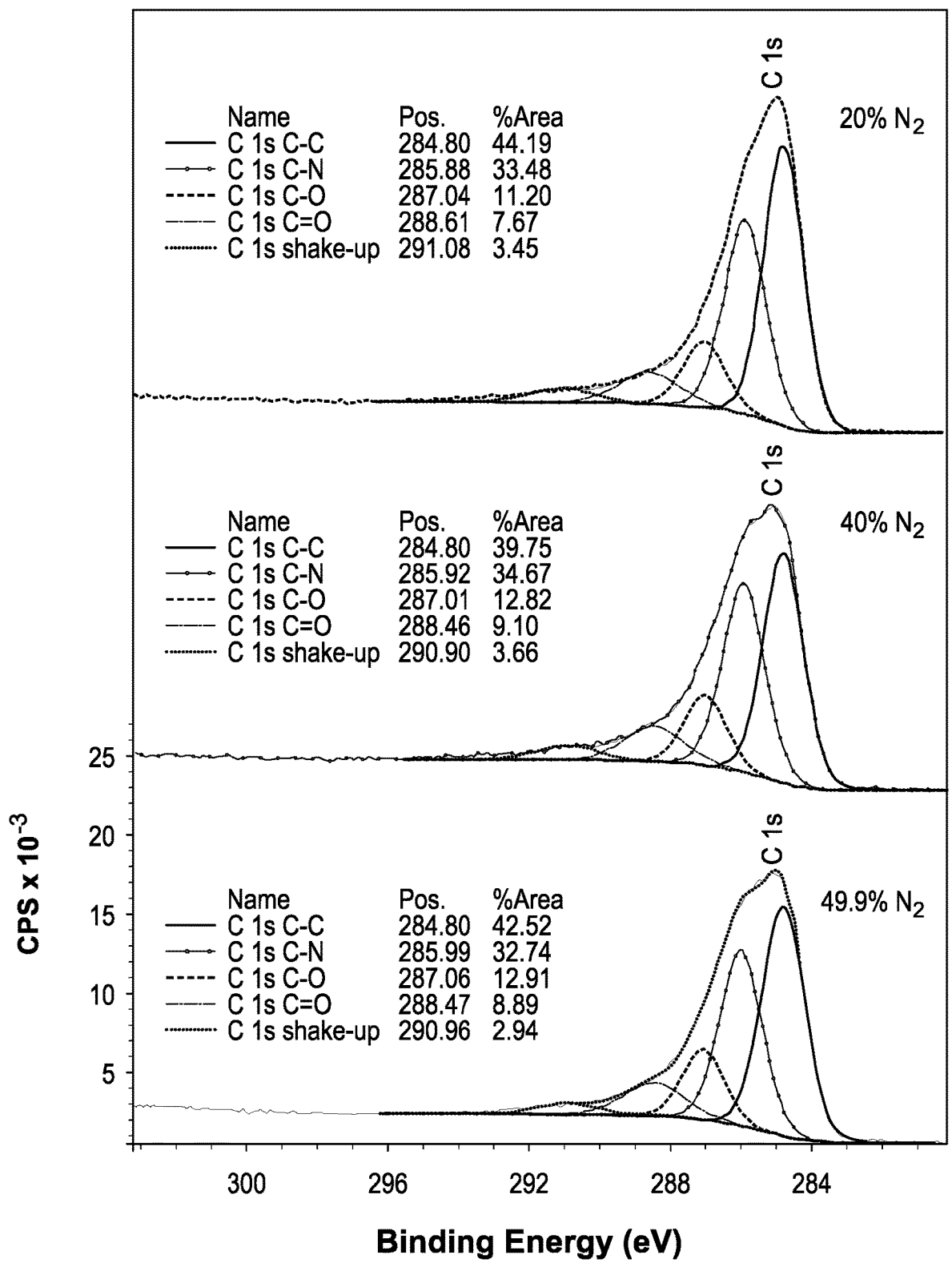
FIG. 8 is a series of plots of X-ray photoelectron spectra testing for different nitrogen content levels.
Figure 9:
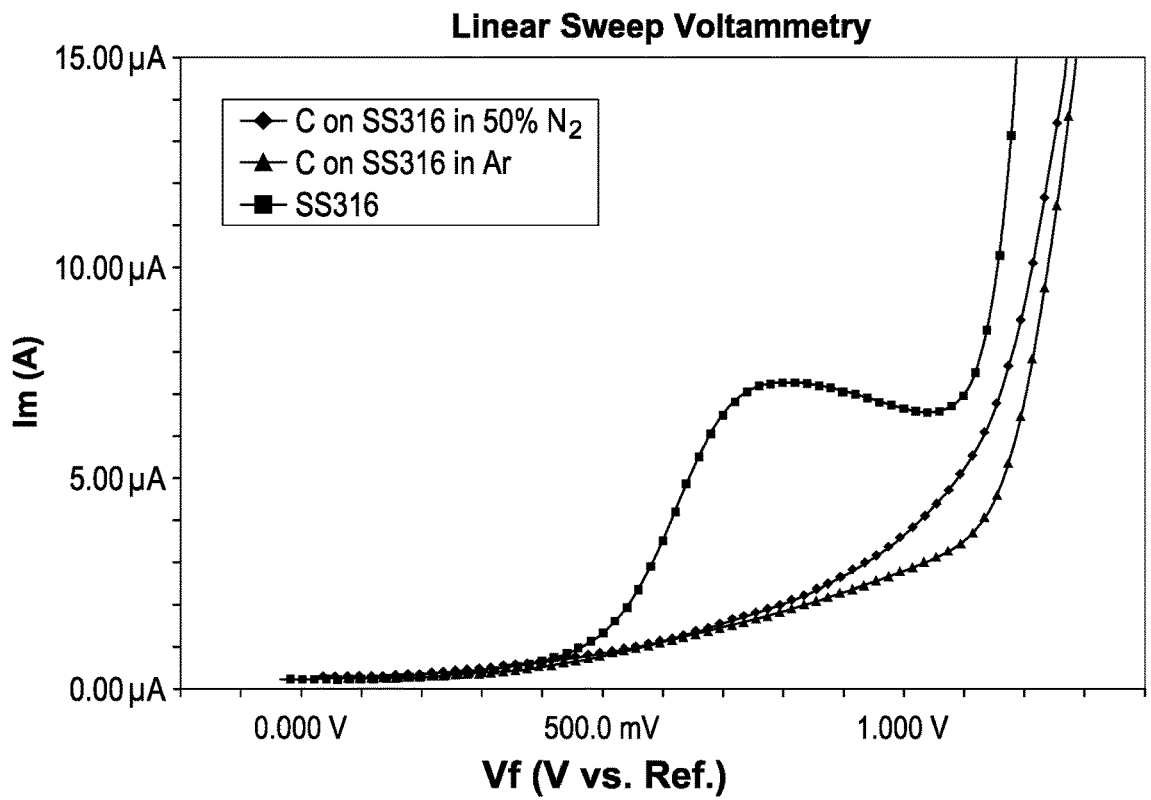
FIG. 9 is a graph depicting a linear sweep voltammogram plot of thin-film electrodes comparing stainless steel 316 without a carbon layer, capped with carbon sputtered in Ar, and capped with carbon sputtered in a 50/50 Ar/N2 mix (based on partial pressure) in mediator-free buffer solutions.
Figure 10:
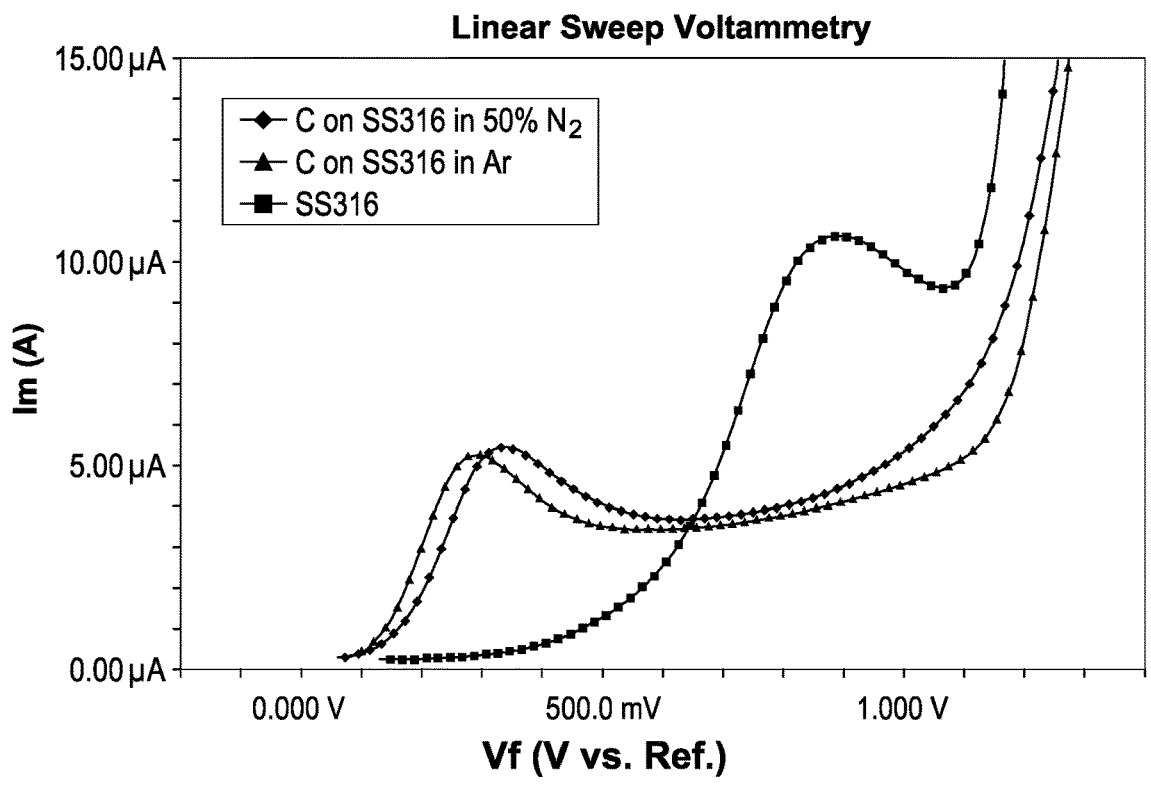
FIG. 10 is a graph depicting a linear sweep voltammogram plot of thin-film electrodes comparing stainless steel 316 without a carbon layer, capped with carbon sputtered in Ar, and capped with carbon sputtered in a 50/50 Ar/N2 mix (based on partial pressure) Fe(II)[CN]6 mediator-containing buffer solutions.
Figure 11:
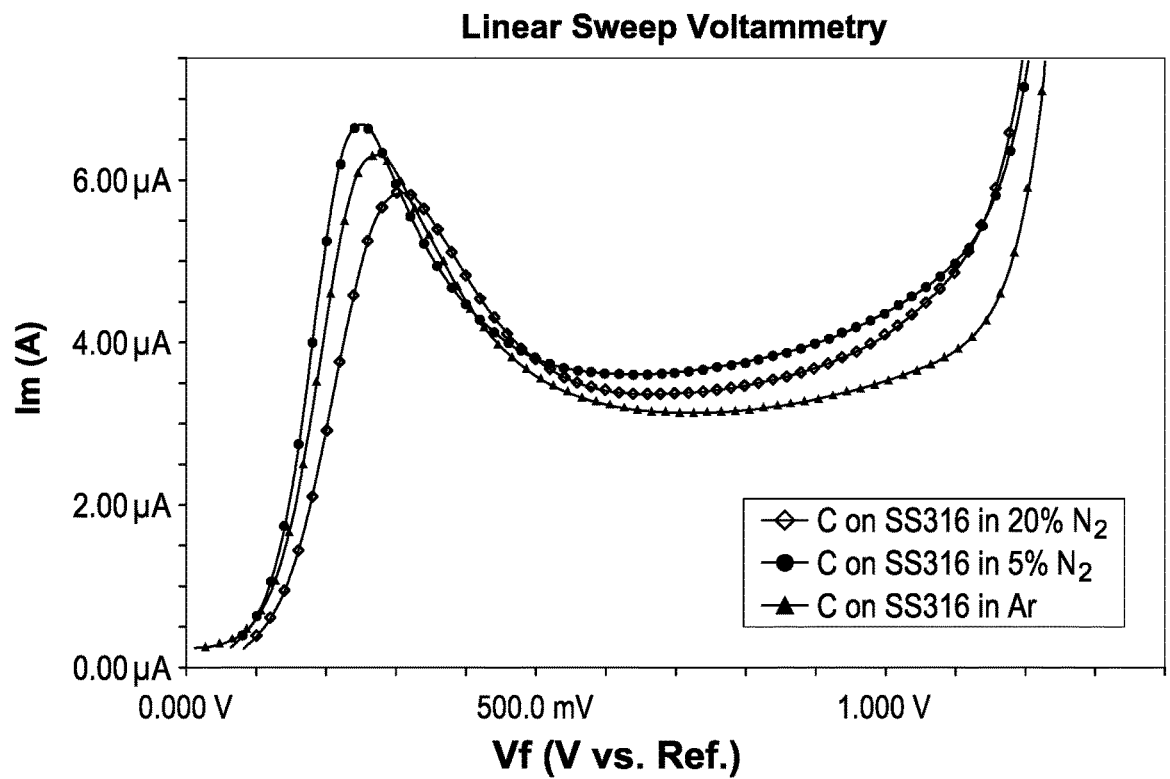
FIG. 11 is a graph depicting a linear sweep voltammogram plot of thin-film electrodes comparing stainless steel 304 capped with carbon sputtered in Ar, capped with carbon sputtered in an 80/20 Ar/N2 mix (based on partial pressure), and capped with carbon sputtered in a 50/50 Ar/N2 mix (based on partial pressure), in Fe(II)[CN]6 mediator-containing buffer solutions.

Thin film electrodes having a conductive layer sputtered from a SS304 source and carbon-containing layers sputtered in an Ar and $N_2$ gas mixture atmosphere having various concentrations of $N_2$ were analyzed by Carbon envelope X-ray photoelectron spectra to investigate the composition of the carbon-containing film layer as a function of nitrogen concentration in the sputtering atmosphere. All samples were sputtered on a SS304 conductive layer generated in a roll-to-roll production machine. The results are shown in FIGS. 7 and 8. A review of FIGS. 7 and 8 reveals that the introduction and growth of a carbon-nitride species following the introduction of $N_2$ into the sputtering chamber and that the C—N species concentration remains relatively constant above a nitrogen concentration of about 5% by partial pressure.

Example 11—Application of Type 1 Linear Sweep Voltammetry Test to Thin-Film Electrodes Different thin-film electrodes were tested using the Type 1 Linear Sweep Voltammetry Test. In more detail, thin-film electrodes formed with a stainless steel 316 (SS316) conductive layer, including an electrode without a resistive material layer, an electrode with an amorphous carbon layer deposited thereon in a pure Ar atmosphere, and an electrode with an amorphous carbon-containing layer deposited thereon in a 50% nitrogen atmosphere were tested. The electrodes were all produced in a batch experimental unit.

Anodic polarization scans in potassium phosphate buffer solution (PBS) at 25 mV/s using a saturated calomel (SCE) reference electrode and each of the SS316 thin film electrodes as the working electrode. The results are illustrated graphically in FIG. 9. A review of FIG. 9 reveals that the anodic break down current of the electrode is significantly suppressed by the introduction of the carbon containing layer on top of the SS316 layer, whether produced in pure Ar or 50% nitrogen. Any background current from approximately 0 to +500 mV (vs SCE) can interfere with electrochemical measurements when this material is used in a blood glucose sensor.

Anodic polarization scans in PBS, with 1 mM K4[FeII(CN)6] redox mediator added, at 25 mV/s using a saturated calomel (SCE) reference electrode and each of the SS316 thin film electrodes as the working electrode. The results are illustrated graphically in FIG. 10 and illustrates the heterogeneous electron transfer kinetics with the Fe(II)[CN]6 mediator for these electrodes as indicated by the voltage at which oxidation of Fe(II)[CN]6 occurs. It can be generally desirable for the thin-film electrodes used in biosensors to exhibit a peak anodic current for Fe(II)[CN]6 that occurs at a voltage as low as possible. It can also generally be desirable for the thin-film electrodes used in biosensors to exhibit minimized and/or reduced currents under the influence of certain electrode potentials. A review of FIG. 10 reveals that the electron transfer kinetics of the electrode with the redox mediator are significantly increased when the carbon containing layer is sputtered in either a pure Ar or 50% $N_2$ atmosphere. This plot shows that the carbon-nitride containing film maintains its electrochemical performance required for a biosensor while having the advantage over carbon sputtered in Ar because of its increased deposition rate and scratch resistance.

Example 12—Application of Type 1 Linear Sweep Voltammetry Test to Thin-Film Electrodes Different thin-film electrodes were tested using the Type 1 Linear Sweep Voltammetry Test. In more detail, thin-film electrodes formed with a stainless steel 304 (SS304) conductive layer, including an electrode with an amorphous carbon layer deposited thereon in a pure Ar atmosphere, an electrode with an amorphous carbon-containing layer deposited thereon in a 20% nitrogen atmosphere, and an electrode with an amorphous carbon-containing layer deposited thereon in a 50% nitrogen atmosphere were tested. The electrodes were all produced in a roll-to-roll sputter coater.

Anodic polarization scans in PBS, with 1 mM K4[FeII(CN)6] redox mediator added, at 25 mV/s using a saturated calomel (SCE) reference electrode and each of the SS304 electrodes as the working electrode. The results are illustrated graphically in FIG. 11. A review of FIG. 11 reveals that the electron transfer kinetics between the mediator and electrode are slightly faster when the carbon layer is sputtered in a pure Ar atmosphere, compared to a $N_2$ containing atmosphere. However, even the films sputtered in a 1:1 Ar:$N_2$ gas mixture is still useful in a biosensor and has an increase in deposition rate of ~164% compared to carbon sputtered in pure Ar.

Example 13—Application of Type 1 Cyclic Voltammetry Test to Thin-Film Electrodes Different thin-film electrodes were tested using the Type 1 Cyclic Voltammetry Test. In more detail, thin-film electrodes formed with a stainless steel 304 (SS304) conductive layer and capped with a carbon containing layer sputtered in an atmosphere of N2 that ranged from 0, 5, 10, 15, 20, 40, and 50% N2 by partial pressure, respectively. The electrodes were all produced in a roll-to-roll sputter coater.

Figure 12:
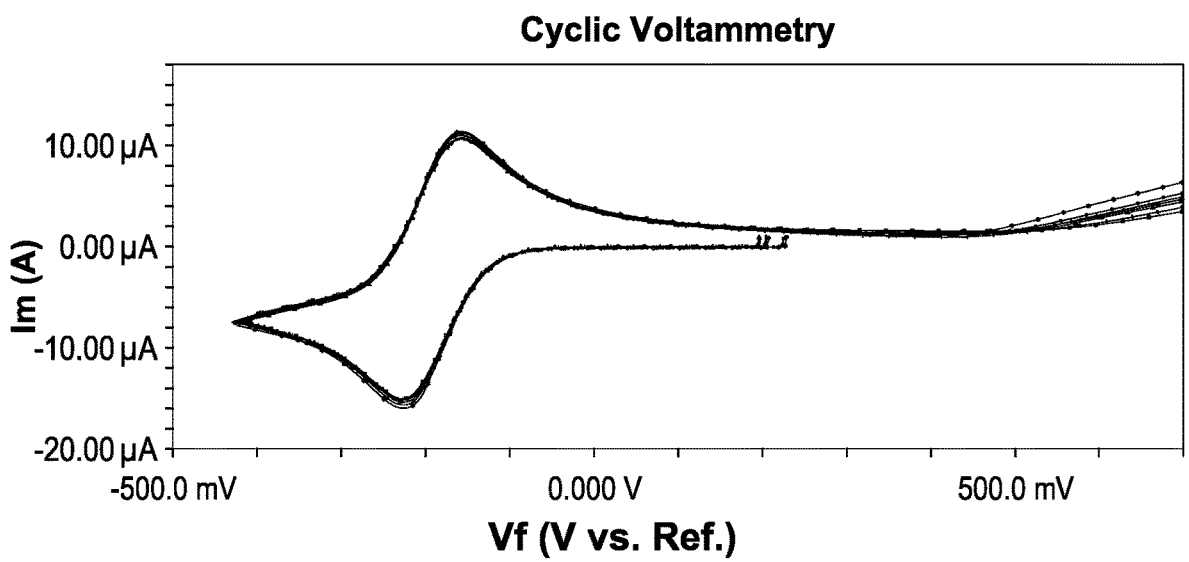
FIG. 12 is a graph depicting a cyclic voltammogram plot of thin-film electrodes comparing stainless steel 304 capped with carbon sputtered in mixed Ar and N2 atmospheres containing 0, 5, 10, 15, 20, 40, and 50% N2 (based on partial pressure), respectively, in [RuIII(NH3)6]Cl3 mediator-containing buffer solutions.

Cyclic voltammograms in PBS, with 2 mM [RuIII(NH3)6]Cl3 mediator added, at 25 mV/s using a saturated calomel (SCE) reference electrode and each of the SS304 electrodes as the working electrode. The results are illustrated graphically in FIG. 12. A review of FIG. 12 reveals that the electron transfer kinetics between the mediator and electrode are not affected by the introduction of N2 into the sputtering chamber when [RuIII(NH3)6]Cl3 is used as the redox mediator. This is unexpected because the electron transfer kinetics with a $K_4[Fe^{II}(CN)_6]$ redox mediator are slightly negatively affected by the introduction of N2 into the sputtering chamber during carbon deposition.

Example 14—Coefficient of Friction Analysis of Thin Film Electrodes

Different thin-film electrodes were tested to determine the coefficient of friction as a function of increasing normal force on the coated surface. In more detail, thin-film electrodes formed with a stainless steel 316 (SS316) conductive layer, including an electrode without a resistive material layer, an electrode with an amorphous carbon layer deposited thereon in a pure Ar atmosphere, and an electrode with an amorphous carbon-containing layer deposited thereon in a 21% nitrogen atmosphere were tested. The electrodes were all produced in a batch experimental unit.

Figure 13:
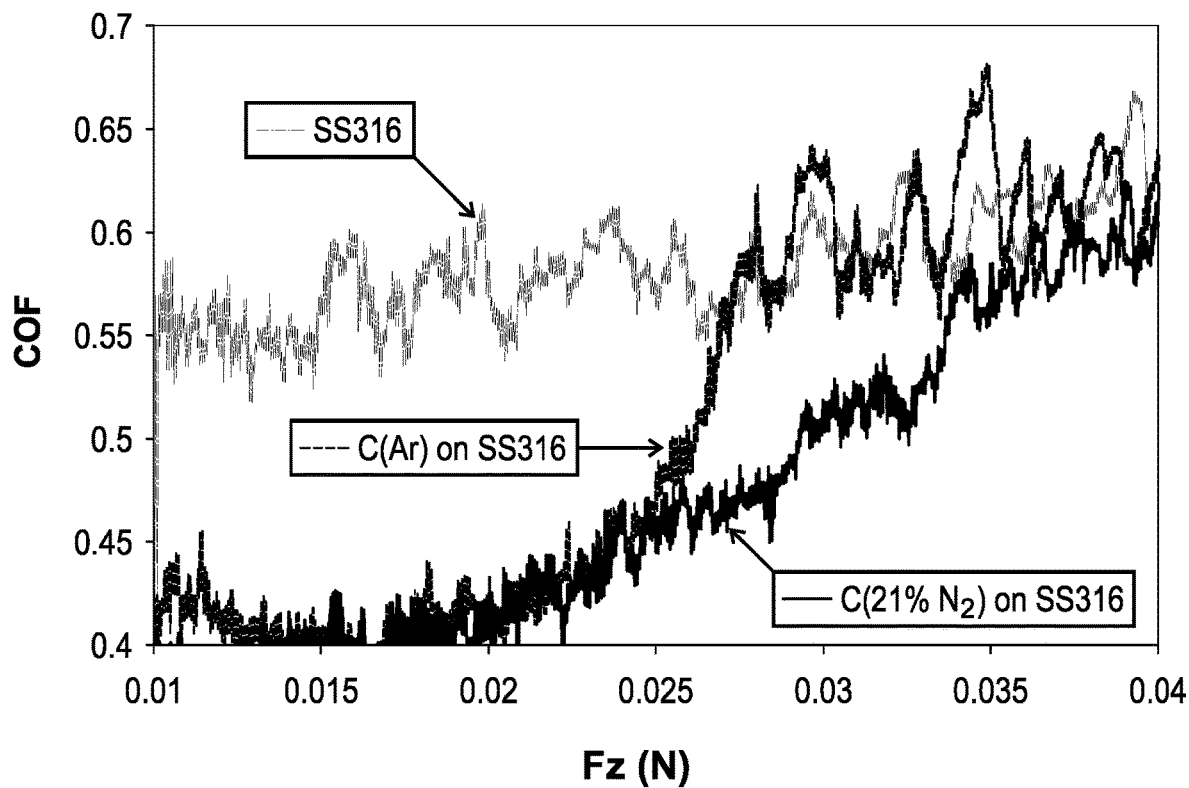
FIG. 13 is a graph showing a plot of coefficient of friction as a function of normal force for thin-film electrodes comparing stainless steel 316 without a carbon layer, capped with carbon sputtered in Ar, and capped with carbon sputtered in a 79/21 Ar/N2 mix (based on partial pressure)

The coefficient of friction (COF) versus the normal force was determined for each of thin film SS316 electrodes. The results are illustrated graphically in FIG. 13. A review of FIG. 13 reveals that the electrode with the SS316 conductive layer alone had a much higher COF compared to the carbon capped films. This shows that the carbon capped films are more durable. The SS316 also appears to be more brittle compared to the carbon films as can be seen by the noisiness of the trace. In addition, FIG. 13 shows that the carbon containing film sputtered in 21% N2 is a tougher film, which shows a higher tolerance to cracking compared to the carbon sputtered in pure Ar. This is evident by the step change in COF, which is indicative of the carbon layer cracking and exposing the SS316 layer, being at higher normal forces for the carbon sputter in 21% N2 compared to that of carbon sputtered in pure Ar.

Figure 14:
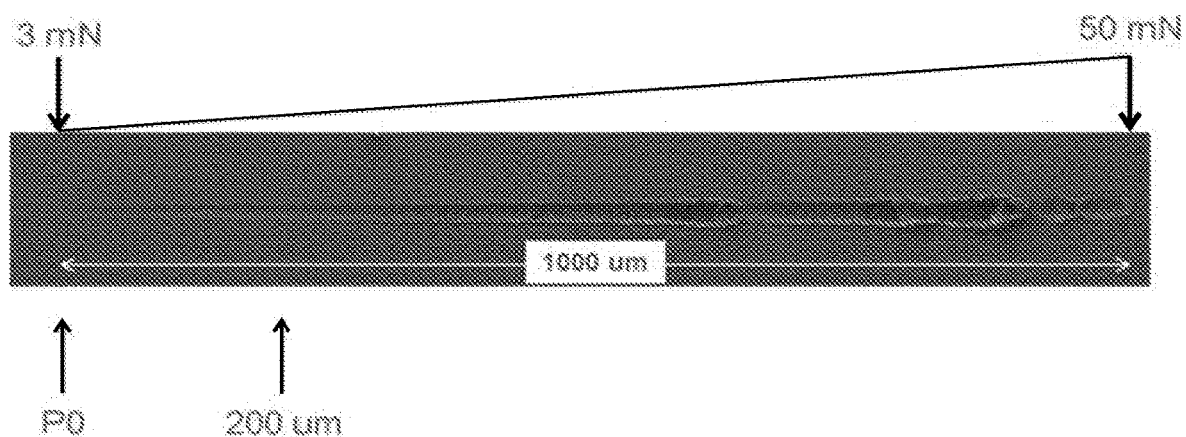
FIG. 14 is an illustration depicting the gradient normal force application as a function of distance for the thin-film nano-scratch testing.
Figure 15A:
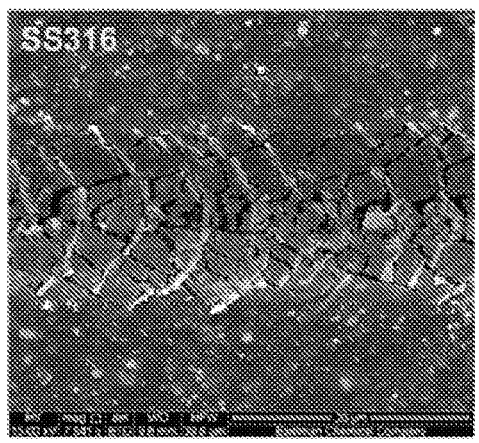
FIGS. 15 A-C are images showing the nano-scratch testing results for thin-film electrodes comparing stainless steel 316 without a carbon layer, capped with carbon sputtered in Ar, and capped with carbon sputtered in a 79/21 Ar/N2 mix (based on partial pressure), at the 200 micron distance.
Figure 15B:
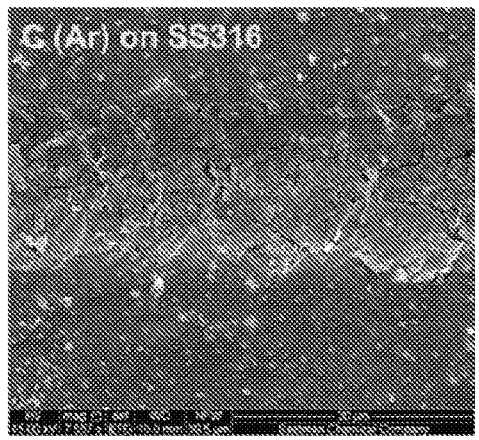
Figure 15C:
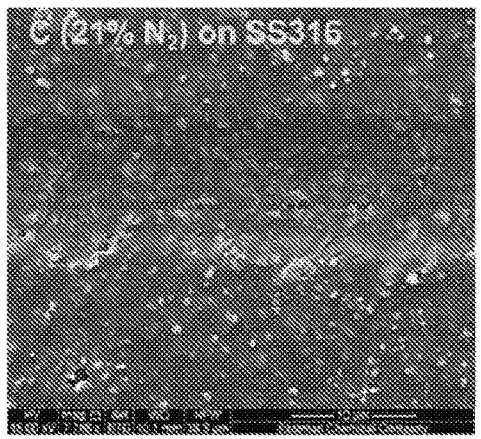

Example 15—Mechanical Toughness (Resistance to Cracking) Analysis of Thin Film Electrodes The scratch resistance was evaluated for each of the thin film SS316 electrodes according to Example 8 by subjecting them to nano-scratch testing following a gradient normal force application from 3 mN to ~10 mN, as illustrated in FIG. 14. The results of the nano-scratch test are shown in the images in FIGS. 15 A-C, where these images were taken 200 µm from the initial scratch point. A review of FIGS. 15 A-C reveals that the SS316 and SS316 capped with carbon sputtered in pure Ar have significant cracking, with the SS316 film having the most cracking. However, the SS316 capped with carbon sputtered in 21% $N_2$ still shows resistance to cracking at this normal force.

The above detailed description of embodiments of the disclosure is intended to describe various aspects of the invention in sufficient detail to enable those skilled in the art to practice the invention. Other embodiments can be utilized and changes can be made without departing from the scope of the invention. The above detailed description is, therefore, not to be taken in a limiting sense. The scope of the present invention is defined only by claims presented in subsequent regular utility applications, along with the full scope of equivalents to which such claims are entitled.

In this description, references to "one embodiment," "an embodiment," or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, step, etc. described in one embodiment may also be included in other embodiments, but is not necessarily included. Thus, the present technology can include a variety of combinations and/or integrations of the embodiments described herein.

The inventors hereby state their intent to rely on the Doctrine of Equivalents to determine and assess the reasonably fair scope of the present disclosure as it pertains to any apparatus not materially departing from but outside the literal scope of the invention as set forth in the following claims.

Definitions

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "include," and "included" have the same open-ended meaning as "comprising," "comprises," and "comprise" provided above.'

NUMERICAL RANGES

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

What is claimed is:

1. An electrochemical electrode for use in a biosensor, said electrode comprising:
   a substrate comprising a flexible, electrically-non-conductive polymer film;
   an electrically-conductive layer deposited on said substrate; and
   an electrically-resistive material layer deposited on said conductive layer;
   wherein said electrically-resistive material layer comprises amorphous carbon and at least one C—N species; and
   wherein said C—N species is present in an amount of at least 20 atomic percentage based on the total electrically-resistive material layer.

2. The electrochemical electrode according to claim 1, wherein the electrically-conductive layer comprises nickel and chromium,
   wherein a combined weight percent of the nickel and chromium in the electrically-conductive layer is in the range of 25 to 100 weight percent, based on the total weight of the electrically-conductive layer equaling 100 weight percent.

3. The electrochemical electrode according to claim 1, wherein the electrically-conductive layer comprises greater than 20 weight percent chromium.

4. The electrochemical electrode according to claim 3, wherein the balance of the electrically-conductive layer is nickel.

5. The electrochemical electrode according to claim 1, wherein the electrically-conductive layer comprises nickel, chromium and iron,
   wherein a combined weight percent of the nickel and chromium in the electrically-conductive layer is in the range of 25 to less than 95 weight percent,
   wherein the weight percent of nickel in the electrically-conductive layer is at least 4 weight percent,
   wherein the weight percent of chromium in the electrically-conductive layer is at least 10 weight percent,
   wherein the weight percent of iron in the electrically-conductive layer at least 2 weight percent, and
   wherein the electrically-conductive layer comprises 0 to 20 weight percent molybdenum.

6. The electrochemical electrode according to claim 1, wherein the weight percent of nickel in the electrically-conductive layer is in the range from about 8 to about 81 weight percent.

7. The electrochemical electrode according to claim 1, wherein the weight percent of chromium in the electrically-conductive layer is in the range from about 14 to about 21 weight percent.

8. The electrochemical electrode according to claim 1, wherein the weight percent of iron in the electrically-conductive layer is in the range from about 6 to about 74 weight percent.

9. The electrochemical electrode according to claim 1, wherein the weight percent of nickel in the electrically-conductive layer is in the range from about 70 to about 81 weight percent.

10. The electrochemical electrode according to claim 1, wherein the weight percent of iron in the electrically-conductive layer is in the range from about 6 to about 10 weight percent.

11. The electrochemical electrode according to claim 1, wherein the weight percent of iron in the electrically-conductive layer is in the range from about 61 to about 75 weight percent.

12. The electrochemical electrode according to claim 1, wherein the electrically-conductive layer comprises 0 to 13 weight percent molybdenum.

13. The electrochemical electrode according to claim 1, wherein the electrically-conductive layer comprises nickel, chromium, iron, and molybdenum,
   wherein the weight percent of nickel in the electrically-conductive layer is in the range of 10 to 30 weight percent,
   wherein the weight percent of chromium in the electrically-conductive layer is in the range of 16 to 26 weight percent,
   wherein the weight percent of iron in the electrically-conductive layer is in the range of 39 to 71 weight percent, and
   wherein the weight percent of molybdenum in the electrically-conductive layer is in the range of 2 to 10 weight percent, all based on the total weight of the electrically-conductive layer equaling 100 weight percent.

14. The electrochemical electrode according to claim 13,
   wherein the weight percent of nickel in the electrically-conductive layer is in the range of 10 to 16 weight percent,
   wherein the weight percent of chromium in the electrically-conductive layer is in the range of 17 to 21 weight percent,
   wherein the weight percent of iron in the electrically-conductive layer is in the range of 55 to 70 weight percent, and
   wherein the weight percent of molybdenum in the electrically-conductive layer is in the range of 2 to 5 weight percent, all based on the total weight of the electrically-conductive layer equaling 100 weight percent.

15. The electrochemical electrode according to claim 13,
   wherein the weight percent of nickel in the electrically-conductive layer is in the range of 12.5 to 29 weight percent,
   wherein the weight percent of chromium in the electrically-conductive layer is in the range of 16 to 24 weight percent, wherein the weight percent of iron in the electrically-conductive layer is in the range of 46 to 66 weight percent, and wherein the weight percent of molybdenum in the electrically-conductive layer is in the range of 3 to 6 weight percent, all based on the total weight of the electrically-conductive layer equaling 100 weight percent.

16. The electrochemical electrode according to claim 13, wherein the weight percent of nickel in the electrically-conductive layer is in the range of 16 to 26.5 weight percent, wherein the weight percent of chromium in the electrically-conductive layer is in the range of 18 to 23 weight percent, wherein the weight percent of iron in the electrically-conductive layer is in the range of 41 to 62 weight percent, and wherein the weight percent of molybdenum in the electrically-conductive layer is in the range of 5 to 8 weight percent, all based on the total weight of the electrically-conductive layer equaling 100 weight percent.

17. The electrochemical electrode according to claim 13, wherein said electrode is a working electrode or a reference electrode or a counter electrode in a biosensor; and wherein the biosensor is a blood glucose sensor.

18. The electrochemical electrode according to claim 13, wherein said electrically-conductive layer is sputtered on said substrate and said electrically-resistive material layer is sputtered on said electrically-conductive layer, and wherein said electrically-resistive material layer is sputtered on said electrically-conductive layer in a nitrogen containing atmosphere.

19. The electrochemical electrode according to claim 13, wherein the nitrogen containing atmosphere comprises a mixture of a noble gas and nitrogen gas.

20. The electrochemical electrode according to claim 13, wherein the nitrogen containing atmosphere comprises a mixture of Ar gas and nitrogen gas, and
   wherein the nitrogen is present in an amount from 5% to 50% based on partial pressure.

* * * * *